(12) United States Patent
Ekwuribe et al.

(10) Patent No.: US 7,713,932 B2
(45) Date of Patent: *May 11, 2010

(54) CALCITONIN DRUG-OLIGOMER CONJUGATES, AND USES THEREOF

(75) Inventors: Nnochiri N. Ekwuribe, Cary, NC (US); Balasingam Radhakrishnan, Chapel Hill, NC (US)

(73) Assignee: Biocon Limited, Electronic (IN)

( * ) Notice: Subject to any disclaimer, the term of this patent is extended or adjusted under 35 U.S.C. 154(b) by 485 days.

This patent is subject to a terminal disclaimer.

(21) Appl. No.: 10/166,355

(22) Filed: Nov. 8, 2002

(65) Prior Publication Data

US 2004/0091452 A1 May 13, 2004

Related U.S. Application Data

(63) Continuation-in-part of application No. 09/873,777, filed on Jun. 4, 2001, now Pat. No. 6,713,452.

(51) Int. Cl.
A61K 38/17 (2006.01)
(52) U.S. Cl. .................. 514/12; 424/78.37; 530/307
(58) Field of Classification Search .............. None
See application file for complete search history.

(56) References Cited

U.S. PATENT DOCUMENTS

| | | | |
|---|---|---|---|
| 3,256,153 A | 6/1966 | Heimlech .................. 424/497 |
| 3,868,356 A | 2/1975 | Smyth ...................... 530/303 |
| 3,919,411 A | 11/1975 | Glass et al. ............... 424/78.27 |
| 3,950,517 A | 4/1976 | Lindsay et al. ................ 514/3 |
| 4,003,792 A | 1/1977 | Mill et al. .................. 530/303 |
| 4,044,196 A | 8/1977 | Huper et al. ................ 526/271 |
| 4,087,390 A | 5/1978 | Shields ................... 525/54.11 |
| 4,093,574 A | 6/1978 | Shields ................... 525/54.11 |
| 4,100,117 A | 7/1978 | Shields ................... 525/54.11 |
| 4,179,337 A | 12/1979 | Davis et al. |
| 4,223,163 A | 9/1980 | Guilloty |
| 4,229,438 A | 10/1980 | Fujino et al. ................. 514/15 |
| 4,253,998 A | 3/1981 | Sarantakis ............... 525/54.11 |
| 4,277,394 A | 7/1981 | Fujino et al. ............... 530/330 |
| 4,338,306 A | 7/1982 | Kitao et al. .................... 514/4 |
| 4,348,387 A | 9/1982 | Brownlee et al. .............. 514/4 |
| 4,410,547 A | 10/1983 | Ueno et al. ................. 514/557 |
| 4,469,681 A | 9/1984 | Brownlee et al. .............. 514/4 |
| 4,472,382 A | 9/1984 | Labrie et al. ................. 514/15 |
| 4,526,938 A | 7/1985 | Churchill et al. |
| 4,554,101 A | 11/1985 | Hopp .......................... 514/2 |
| 4,579,730 A | 4/1986 | Kidron et al. .................. 514/3 |
| 4,585,754 A | 4/1986 | Meisner et al. ................ 514/8 |
| 4,662,392 A | 5/1987 | Vadasz .................. 137/533.11 |
| 4,684,524 A | 8/1987 | Eckenhoff et al. ............ 424/69 |
| 4,698,264 A | 10/1987 | Steinke .................. 428/402.2 |
| 4,717,566 A | 1/1988 | Eckenhoff et al. ........... 424/438 |
| 4,772,471 A | 9/1988 | Vanlerberghe et al. ....... 424/450 |
| 4,774,976 A | 10/1988 | Janecke et al. ................ 137/14 |
| 4,797,288 A | 1/1989 | Sharma et al. .............. 424/476 |
| 4,801,575 A | 1/1989 | Pardridge |
| 4,839,341 A | 6/1989 | Massey et al. ................... 514/4 |
| 4,840,799 A | 6/1989 | Appelgren et al. .......... 424/493 |
| 4,849,405 A | 7/1989 | Ecanow ........................ 514/3 |
| 4,917,888 A | 4/1990 | Katre et al. ............. 424/85.91 |
| 4,935,246 A | 6/1990 | Ahrens ...................... 424/490 |
| 4,946,828 A | 8/1990 | Markussen ..................... 514/3 |
| 4,957,910 A | 9/1990 | Sutton et al. ................ 514/182 |
| 4,963,367 A | 10/1990 | Ecanow ..................... 424/485 |
| 4,963,526 A | 10/1990 | Ecanow ........................ 514/3 |
| 4,994,439 A | 2/1991 | Longenecker et al. .......... 514/3 |
| 5,013,556 A | 5/1991 | Woodle et al. .............. 424/450 |
| 5,055,300 A | 10/1991 | Gupta ....................... 424/409 |
| 5,055,304 A | 10/1991 | Makino et al. .............. 424/465 |
| 5,089,261 A | 2/1992 | Nitecki et al. ............. 424/85.2 |
| 5,093,198 A | 3/1992 | Speaker et al. ......... 428/402.21 |
| 5,099,074 A | 3/1992 | Mueller et al. |
| 5,108,568 A | 4/1992 | Van Alstine |
| 5,122,614 A | 6/1992 | Zalipsky |
| 5,157,021 A | 10/1992 | Balschmidt et al. ............ 514/3 |
| 5,162,430 A | 11/1992 | Rhee et al. ................. 525/54.1 |
| 5,164,366 A | 11/1992 | Balschmidt et al. ............ 514/3 |
| 5,202,415 A | 4/1993 | Jonassen et al. ............. 530/303 |
| 5,206,219 A | 4/1993 | Desai ............................ 514/3 |
| 5,283,236 A | 2/1994 | Chiou ........................... 514/2 |
| 5,286,637 A | 2/1994 | Veronese et al. ............. 435/183 |
| 5,292,802 A | 3/1994 | Rhee et al. ................. 525/54.1 |
| 5,298,410 A | 3/1994 | Phillips et al. |

(Continued)

FOREIGN PATENT DOCUMENTS

DE     196 32 440 A1     2/1998

(Continued)

OTHER PUBLICATIONS

"Pharmaceutical Research: Official Journal of the American Association of Pharmaceutical Scientists," 3(6): 318-326 (1986).

(Continued)

Primary Examiner—Christopher R. Tate
Assistant Examiner—Roy Teller
(74) Attorney, Agent, or Firm—Marianne Fuierer; Moore & Van Allen, PLLC

(57) ABSTRACT

Calcitonin drug-oligomer conjugates that include a calcitonin drug coupled to an oligomer including a single polyalkylene glycol moiety consisting of between 4 and 10 polyalkylene glycol subunits are disclosed. Pharmaceutical compositions including such conjugates and methods of treating bone disorders by administering such conjugates are also disclosed.

13 Claims, 7 Drawing Sheets

U.S. PATENT DOCUMENTS

| | | | |
|---|---|---|---|
| 5,304,473 A | 4/1994 | Belagaje et al. | 435/69.7 |
| 5,308,889 A | 5/1994 | Rhee et al. | 523/113 |
| 5,312,808 A | 5/1994 | Shorr et al. | 514/6 |
| 5,320,840 A | 6/1994 | Camble et al. | |
| 5,324,775 A | 6/1994 | Rhee et al. | 525/54.2 |
| 5,328,955 A | 7/1994 | Rhee et al. | 525/54.1 |
| 5,349,052 A | 9/1994 | Delgado et al. | 530/351 |
| 5,359,030 A * | 10/1994 | Ekwuribe | 530/303 |
| 5,405,621 A | 4/1995 | Sipos | 424/490 |
| 5,405,877 A | 4/1995 | Greenwald et al. | |
| 5,413,791 A | 5/1995 | Rhee et al. | 424/422 |
| 5,415,872 A | 5/1995 | Sipos | 424/490 |
| 5,428,128 A | 6/1995 | Mensi-Fattohi et al. | |
| 5,438,040 A | 8/1995 | Ekwuribe | 514/3 |
| 5,444,041 A | 8/1995 | Owen et al. | 514/2 |
| 5,446,091 A | 8/1995 | Rhee et al. | 525/54.1 |
| 5,457,066 A | 10/1995 | Frank et al. | 435/68.1 |
| 5,461,031 A | 10/1995 | De Felippis | 514/4 |
| 5,468,478 A | 11/1995 | Saifer et al. | |
| 5,504,188 A | 4/1996 | Baker et al. | 530/304 |
| 5,506,203 A | 4/1996 | Backstrom et al. | 514/4 |
| 5,518,998 A | 5/1996 | Backstrom et al. | 514/3 |
| 5,523,348 A | 6/1996 | Rhee et al. | 525/54.1 |
| 5,529,915 A | 6/1996 | Phillips et al. | 435/188 |
| 5,545,618 A | 8/1996 | Buckley et al. | 514/12 |
| 5,550,188 A | 8/1996 | Rhee et al. | 525/54.1 |
| 5,567,422 A | 10/1996 | Greenwald | |
| 5,597,797 A | 1/1997 | Clark | 514/12 |
| 5,606,038 A | 2/1997 | Regen | 536/6.5 |
| 5,612,460 A | 3/1997 | Zalipsky | |
| 5,631,347 A | 5/1997 | Baker et al. | 530/303 |
| 5,637,749 A | 6/1997 | Greenwald | |
| 5,643,575 A | 7/1997 | Martinez et al. | |
| 5,646,242 A | 7/1997 | Baker et al. | 530/303 |
| 5,650,388 A | 7/1997 | Shorr et al. | 514/6 |
| 5,658,878 A | 8/1997 | Backstrom et al. | 514/3 |
| 5,681,567 A | 10/1997 | Martinez et al. | 424/178.1 |
| 5,681,811 A | 10/1997 | Ekwuribe | |
| 5,693,609 A | 12/1997 | Baker et al. | 514/3 |
| 5,693,769 A | 12/1997 | Kahne et al. | 536/5 |
| 5,700,904 A | 12/1997 | Baker et al. | 530/305 |
| 5,707,648 A | 1/1998 | Yiv | 424/450 |
| 5,714,639 A | 2/1998 | Bowman et al. | |
| 5,738,846 A | 4/1998 | Greenwald et al. | 424/85.7 |
| 5,747,445 A | 5/1998 | Backstrom et al. | 514/4 |
| 5,747,642 A | 5/1998 | De Felippis | 530/304 |
| 5,750,497 A | 5/1998 | Havelund et al. | 514/3 |
| 5,763,396 A | 6/1998 | Weiner et al. | 514/3 |
| 5,766,620 A | 6/1998 | Heiber et al. | 424/436 |
| 5,773,581 A | 6/1998 | Camble et al. | |
| 5,824,638 A | 10/1998 | Burnside et al. | 514/3 |
| 5,830,853 A | 11/1998 | Backstrom et al. | 514/4 |
| 5,830,918 A | 11/1998 | Sportsman et al. | 514/648 |
| 5,843,866 A | 12/1998 | Parker et al. | 504/116 |
| 5,849,860 A | 12/1998 | Hakimi et al. | 528/370 |
| 5,853,748 A | 12/1998 | New | 424/439 |
| 5,854,208 A | 12/1998 | Jones et al. | |
| 5,856,451 A | 1/1999 | Olsen et al. | 530/402 |
| 5,866,538 A | 2/1999 | Norup et al. | 514/3 |
| 5,866,584 A | 2/1999 | Cincotta et al. | 514/288 |
| 5,874,111 A | 2/1999 | Maitra et al. | 424/499 |
| 5,898,028 A | 4/1999 | Jensen et al. | 514/4 |
| 5,902,588 A | 5/1999 | Greenwald et al. | 424/278.1 |
| 5,905,140 A | 5/1999 | Hansen | 530/303 |
| 5,907,030 A | 5/1999 | Shen et al. | 530/331 |
| 5,922,675 A | 7/1999 | Baker et al. | 514/4 |
| 5,932,462 A | 8/1999 | Harris et al. | 435/188 |
| 5,942,248 A | 8/1999 | Barnwell | 424/457 |
| 5,948,751 A | 9/1999 | Kimer et al. | 514/4 |
| 5,952,008 A | 9/1999 | Backstrom et al. | 424/499 |
| 5,952,297 A | 9/1999 | De Felippis et al. | 514/3 |
| 5,962,267 A | 10/1999 | Shin et al. | 435/69.4 |
| 5,968,549 A | 10/1999 | New et al. | 424/450 |
| 5,969,040 A | 10/1999 | Hallahan et al. | 525/54.1 |
| 5,981,709 A | 11/1999 | Greenwald et al. | 530/351 |
| 5,985,263 A | 11/1999 | Lee et al. | 424/85.2 |
| 6,004,574 A | 12/1999 | Backstrom et al. | 424/434 |
| 6,011,008 A | 1/2000 | Domb et al. | |
| 6,025,325 A | 2/2000 | Campfield et al. | 514/2 |
| 6,034,054 A | 3/2000 | De Felippis et al. | 514/4 |
| 6,042,822 A | 3/2000 | Gilbert et al. | 424/85.7 |
| 6,043,214 A | 3/2000 | Jensen et al. | 514/3 |
| 6,051,551 A | 4/2000 | Hughes et al. | 514/3 |
| 6,057,292 A | 5/2000 | Cunningham et al. | 514/12 |
| 6,063,761 A | 5/2000 | Jones et al. | 514/3 |
| 6,093,391 A | 7/2000 | Kabanov et al. | 424/85.1 |
| 6,113,906 A | 9/2000 | Greenwald et al. | |
| 6,165,976 A | 12/2000 | Backstrom et al. | 514/3 |
| 6,177,087 B1 | 1/2001 | Greenwald et al. | 424/278.1 |
| 6,191,105 B1 | 2/2001 | Ekwuribe et al. | 514/3 |
| 6,200,602 B1 | 3/2001 | Watts et al. | 424/463 |
| 6,211,144 B1 | 4/2001 | Havelund | 514/4 |
| 6,248,363 B1 | 6/2001 | Patel et al. | 424/497 |
| 6,251,856 B1 | 6/2001 | Markussen et al. | 514/3 |
| 6,258,377 B1 | 7/2001 | New et al. | 424/450 |
| 6,268,335 B1 | 7/2001 | Brader | 514/3 |
| 6,306,440 B1 | 10/2001 | Backstrom et al. | 424/499 |
| 6,309,633 B1 | 10/2001 | Ekwuribe et al. | 424/85.1 |
| 6,310,038 B1 | 10/2001 | Havelund | 514/4 |
| 6,323,311 B1 | 11/2001 | Liu et al. | 530/303 |
| 6,335,316 B1 | 1/2002 | Hughes et al. | 514/3 |
| 6,342,225 B1 | 1/2002 | Jones et al. | 424/193.1 |
| 6,352,974 B1 | 3/2002 | Ghirri et al. | |
| 6,506,730 B1 | 1/2003 | Lee et al. | |
| 6,713,452 B2 * | 3/2004 | Ekwuribe et al. | 514/21 |
| 2002/0160938 A1 | 10/2002 | Brandenburg et al. | 514/3 |
| 2003/0004304 A1 | 1/2003 | Ekwuribe et al. | 528/425 |
| 2003/0027748 A1 | 2/2003 | Ekwuribe et al. | 514/3 |
| 2003/0027995 A1 | 2/2003 | Ekwuribe et al. | 530/399 |
| 2003/0050228 A1 | 3/2003 | Ekwuribe et al. | |
| 2003/0060606 A1 | 3/2003 | Ekwuribe et al. | |
| 2003/0069170 A1 | 4/2003 | Soltero et al. | 514/2 |
| 2003/0083232 A1 | 5/2003 | Soltero et al. | 514/3 |
| 2003/0087808 A1 | 5/2003 | Soltero et al. | 514/3 |
| 2003/0144468 A1 | 7/2003 | Ekwuribe et al. | 528/425 |
| 2003/0153488 A1 | 8/2003 | May et al. | |
| 2004/0017387 A1 | 1/2004 | Soltero et al. | |

FOREIGN PATENT DOCUMENTS

| | | | |
|---|---|---|---|
| EP | 0 031 567 | | 7/1981 |
| EP | 0 092 918 A2 | | 11/1983 |
| EP | 0 354 855 A2 | | 2/1990 |
| EP | 0 381 070 A1 | | 8/1990 |
| EP | 0483465 B1 | | 5/1992 |
| EP | 0 511 903 A2 | | 11/1992 |
| EP | 0 483 465 | | 8/1995 |
| EP | 0 597 007 | | 10/1996 |
| EP | 0 621 777 | | 11/1996 |
| EP | 0797615 B1 | | 1/1997 |
| EP | 0 822 218 A2 | | 2/1998 |
| GB | 1 492 997 | | 11/1977 |
| JP | 01207320 | | 8/1989 |
| JP | 1 254 699 | | 10/1989 |
| WO | WO93/01802 | | 2/1993 |
| WO | WO 94/23740 | | 10/1994 |
| WO | WO95/09831 | | 4/1995 |
| WO | WO95/30641 | | 11/1995 |
| WO | WO97/14740 | | 4/1997 |
| WO | WO 97/14740 * | 4/1997 | 530/303 |
| WO | WO98/07745 | | 2/1998 |
| WO | WO99/32134 | | 7/1999 |
| WO | WO99/65941 | | 12/1999 |
| WO | WO 00/43034 | | 7/2000 |

| | | |
|---|---|---|
| WO | WO 00/78302 A1 | 12/2000 |
| WO | WO 01/12230 | 2/2001 |
| WO | WO 02/09766 A1 | 2/2002 |
| WO | WO 02/098232 A1 | 12/2002 |
| WO | WO 02/098446 A1 | 12/2002 |
| WO | WO 03/022208 A2 | 3/2003 |
| WO | WO 03/022210 A2 | 3/2003 |
| WO | WO 03/022210 A3 | 3/2003 |
| WO | WO 03/022996 A2 | 3/2003 |

OTHER PUBLICATIONS

Banting et al., "Pancreatic Extracts in the Treatment of Diabetes Mellitus," *Can. Med. Assoc. J.*, 12: 141-146 (1922).
Coudert et al., "A Novel, Unequivocal Synthesis of Polyethylene Glycols," *Synthetic Communications*, 16(1): 19-26 (1986).
Francis, G.E., et al., Polyethylene Glycol Modification: Relevance of Improved Methodology to Tumour Targeting, *Journal of Drug Targeting*, vol. 3, pp. 321-340 (1996).
Guzman, Angel, et al., Effects of Fatty Ethers and Stearic Acid of the Gastrointestinal Absorption of Insulin, *PRHSJ*, vol. 9, No. 2, pp. 155-159 (Aug. 1990).
H. Allcock & F. Lampe, "Contemporary Polymer Chemistry," 394-403 (2nd. ed., 1991).
J. Milton Harris, "Laboratory Synthesis of Polyethylene Glycol Derivatives," *J. Macromol. Science—Rev. Macromol. Chem. Phys.*, C25(3): 325-373 (1985).
Krishnan, B. Radha, et al., Stability and Physical Characteristics of Orally Active Amphiphilic Human Insulin Analog, Methoxy (Polyethylene Glycol) Hexanoyl Human Recombinant Insulin (HIM2), *Proceed. Int'l. Symp. Control. Rel. Bioact. Mater.*, vol. 27 pp. 1038-1039 (2000).
Lindsay, D.G., et al., The Acetylation of Insulin, *Biochem J.*, vol. 121, pp. 737-745 (1971).
Mesiha, M.S., et al., Hypoglycaemic effect of oral insulin preparations containing Brij 35, 52, 58 or 92 and stearic acid, *J. Pharm. Pharmacol.*, vol. 33, pp. 733-734 (1981).
Moghaddam, Amir, Use of polyethylene glycol polymers for bioconjugations and drug development, *American Biotechnology Laboratory*, pp. 42, 44 (Jul. 2001).
Neubauer, H. Paul, et al., Influence of Polyethylene Glycol Insulin on Lipid Tissues of Experimental Animals, *Diabetes*, vol. 32, pp. 953-958 (Oct. 1983).
Shen, Wei-Chiang, et al., (C) Means to Enhance Penetration; (3) Enhancement of polypeptide and protein absorption by macromolecular carriers via endocytosis and transcytosis, *Advanced Drug Delivery Reviews*, vol. 8, pp. 93-113 (1992).
Sirokman, Geza, et al., Refolding and proton pumping activity of a polyethylene glycolbacteriorhodopsin water-soluble conjugate, *Protein Science*, vol. 2, pp. 1161-1170 (1993).
Torchilin, Vladimir P., Immunoliposomes and PEGylated Immunoliposomes: Possible Use for Targeted Delivery of Imaging Agents, *Immunomethods*, vol. 4, pp. 244-258 (1994).
Wei, Jiang, et al., A Poly(Ethylene Glycol) Water-soluble Conjugate of Porin: Refolding to the Native State, *Biochemistry*, vol. 34, pp. 6408-6415 (1995).
Xia, Jiding, et al., Effects of polyoxyethylene chain length distribution on the interfacial properties of polyethylene glycol n-dodecyl ether, *Yinghong Huaxue*, vol. 2, No. 4, pp. 59-65 (Abstract Only) (1985).
Y. Chen & G. Baker, "Synthesis and Properties of AMA Amphiphiles," *J. Org. Chem.*, 64: 6870-6873 (1999).
Zalipsky, Samuel, et al., Peptide Attachment to Extremities of Liposomal Surface Grafted PEG Chains: Preparation of the Long-Circulating Form of Laminin Pentapeptide, YIGSR, *Bioconjugate Chem.*, vol. 6, pp. 705-708 (1995).
Baudyš et al., "Stabilization and intestinal absorption of human calcitonin," *Journal of Controlled Release* 39: 145-151 (1996).
International Search Report corresponding to PCT/US02/17575; Date of Mailing: Sep. 25, 2002.
Still et al., *Methods of Reducing Hypoglycemic Episodes in the Treatment of Diabetes Mellitus*, U.S. Appl. No. 10/461,199, filed Jun. 13, 2003.

Radhakrishnan et al., *Insulin Polypeptide-Oligomer Conjugates, Proinsulin Polypeptide-Oligomer Conjugates and Methods of Synthesizing Same*, U.S. Appl. No. 10/389,499, filed Mar. 17, 2003.
Soltero et at., *Pharmaceutical Compositions of Insulin Drug-Oligomer Conjugates and Methods of Treating Diseases Therewith*, U.S. Appl. No. 10/382,155, filed Mar. 5, 2003.
Soltero et al., *Pharmaceutical Compositions of Drug-Oligomer Conjugates and Methods of Treating*, U.S. Appl. No. 10/382,069, filed Mar. 5, 2003.
Soltero et al., *Insulin Polypeptide-Oligomer Conjugates, Proinsulin Polypeptide-Oligomer Conjugates and Methods of Synthesizing Same*, U.S. Appl. No. 10/382,022, filed Mar. 5, 2003.
Ekwuribe et al., *Calcitonin Drug-Oligomer Conjugates, and Uses Thereof*, U.S. Appl. No. 10/166,355, filed Nov. 8, 2002, including Preliminary Amendment dated Feb. 26, 2003 and Supplemental Preliminary Amendment dated Mar. 31, 2003.
Ekwuribe et al., *Mixtures of Drug-Oligomer Conjugates Comprising Polyalkylane Glycol, Uses Thereof, And Methods of Making Same*, U.S. Appl. No. 09/873,797, filed Jun. 4, 2001.
Ekwuribe et al., *Hydrophilic and Lipophilic Balanced Microemulsion Formulations of Free-Form and/or Conjugation-Stabilized Therapeutic Agents Such as Insulin*, U.S. Appl. No. 09/614,203, filed Jul. 12, 2000.
Hinds et al., *Synthesis and Characterization of Poly9ethylene glycol)-Insulin*, Bioconjugate Chem., vol. 11, 2000, pp. 195-201.
Ekwuribe et al., *Amphiphilic Prodrugs*, U.S. Appl. No. 09/474,915, filed Dec. 31, 1999.
Abuchowski, A. and F. F. Davis "Soluble Polymer-Enzyme Adducts" pp. 367-383, *Enzymes as Drugs*, Ed. J. S. Holcenberg, John Wiley (1981).
Agarwal et al. "Polymethyacrylate-based Microparticulates of Insulin for Oral Delivery: Preparation and In Vitro Dissolution Stability in the Presence of Enzyme Inhibitors" *International Journal of Pharmaceutics* 225:31-39 (2001).
Akiyama et al. "The Synthesis of New Derivatives of 1-β-D-Arabinofuranosylcytosine" *Chem. Pharm. Bull.* 26(3):981-984 (1978).
Allaudeen et al. "Orally Active Insulin: A Single Insulin Conjugate Selected for Future Studies" 60th Annual Meeting of the American Diabetes Assoc., Atlanta, GA, Jun. 2000 (Abstract).
Anderson et al. "HIM2, a Novel Modified Insulin, has Improved Systemic Pharmacokinetics in Normal Dogs, Compared to Unmodified Insulin" American Diabetes Association 62nd Annual Meeting, Jun. 2002 (Abstract).
Ansell et al. "Application of Oligo-(14-amino-3,6,9,12-tetraoxatetradecanoic acid) Lipid Conjugates as Steric Barrier Molecules in Liposomal Formulations" *Bioconjugate Chem.* 10:653-666 (1999).
Aoshima et al. "$N^4$-Behenoyl-1-β-D-Arabinofuranosylcytosine as a Potential New Antitumor Agent" *Cancer Research* 37:2481-2486 (1977).
Baker, D. C. et al. "Prodrugs of 9-β-D-Arabinofuranosyladenine. 1. Synthesis and Evaluation of Some 5'-(O Acyl) Derivatives" *J. Med. Chem.* 21(12):1218-1221 (1978).
Banting et al. "Pancreatic Extracts in the Treatment of Diabetes Mellitus: Preliminary Report" *Can. Med. Assoc. J.* 145(10):1281-1286 (1991).
Baudys et al. "Stabilization and Intestinal Absorption of Human Calcitonin" *J. Control. Rel.* 39:145-151 (1996).
Baudys et al. "Synthesis and Characterization of Different Glycosylated Derivatives of Insulin" *Proceed Intern Symp. Cont. Rel. Bioactive Mater.* 19:210-211 (1992).
Block, Lawrence H. "Pharmaceutical Emulsions and Microemulsions" *Pharmaceutical Dosage Forms: Disperse Systems* vol. 2, Ed. Lieberman et al., pp. 47-109 (1996).
Boccu et al. "Pharmacokinetic Properties of Polyethylene Glycol Derivatized Superoxide Dismutase" *Pharm. Res. Comm.* 14:113-120 (1982).
Bone et al. "Successful Treatment of an Insulin Dependent Rat Model of Human Type 1 Diabetes with Orally Active Insulin" Program and Abstracts, 4th International Workshop on Lessons from Animal Diabetes, Omiya, Japan, Nov. 1994 (Abstact).

Bone et al. "Successful Treatment of Type 1 Diabetes with Orally-Active Insulin: Studies in The Insulin Dependent BB/S Rat" Program and Abstracts, 55th Annual Meeting of the American Diabetes Association, Atlanta Georgia, Jun. 1995 (Abstract).

Brange and Volund "Insulin Analogs with Improved Pharmacokinetic Profiles" *Advanced Drug Delivery Reviews* 35:307-335 (1999).

Brange et al. "Chemical Stability of Insulin. 1. Hydrolytic Degradation During Storage of Pharmaceutical Preparations" *Pharm. Res.* 9(6):715-726 (1992).

Brange et al. "Chemical Stability of Insulin. 2. Formation of Higher Molecular Weight Transformation Product During Storage of Pharmaceutical Preparations" *Pharm. Res.* 9(6):727-734 (1992).

Brange, J. "Galenics of Insulin: The Physico-Chemical and Pharmaceutical Aspects of Insulin and Insulin Preparations" Novo Research Institute, Denmark, pp. 18-100 (1987).

Chien, Y. W., Novel Drug Delivery Systems, pp. 678-679, Marcell Deffer, Inc., New York, N.Y. (1992).

Cleland et al. "Emerging Protein Delivery Methods" *Current Opinion in Biotechnology* 12:212-219 (2001).

Clement et al. "Effects of Multiple Doses of Orally Administered Hexyl Insulin M2 (HIM2) on Postprandial Blood Glucose (PPG) Concentrations in Type 1 Diabetic (T1) Patients" American Diabetes Association 62nd Annual Meeting, Jun. 2002 (Poster).

Clement et al. "Oral Insulin Product Hexyl-Insulin Monoconjugate 2 (HIM2) in Type 1 Diabetes Mellitus: The Glucose Stabilization Effects of HIM2" *Diabetes Technology & Therapeutics* 4(4):459-466 (2002).

Clement, Stephen "A Dose-Escalation Study of the Effects of Two Sequential Doses of Oral Modified Insulin on Blood Glucose Concentrations in Patients with Type 1 Diabetes Mellitus" American Diabetes Association Annual Meeting (Jun. 25, 2001) (Abstract).

Clement, Stephen "A Dose-Escalation Study of the Effects of Two Sequential Doses of Oral Modified Insulin on Blood Glucose Concentrations in Patients with Type 1 Diabetes Mellitus" American Diabetes Association Annual Meeting (Jun. 25, 2001) (Poster).

Conradi et al. "The Influence of Peptide Structure on Transport Across Caco-2 Cells" *Pharm. Res.* 8(12):1453-1459 (1991).

Coombes et al. "Biodegradable Polymeric Microparticles for Drug Delivery and Vaccine Formulation: the Surface Attachment of Hydrophilic Species Using the Concept of Poly(Ethylene Glycol) Anchoring Segments" *Biomaterials* 18:1153-1161 (1997).

Damge et al. "Poly(alkyl cyanoacrylate) Nanospheres for Oral Administration of Insulin" *Journal of Pharmaceutical Sciences* 86(12):1403-1409 (Dec. 1997).

Dandona et al. "Effect of an Oral Modified Insulin on Blood Glucose Levels in Fasting and Fed Type 1 Diabetic Patients Receiving a 'Basal' Regimen of Injected Insulin" American Diabetes Association Annual Meeting (Jun. 25, 2001) (Abstract).

Delgado et al. "The Uses and Properties of PEG-Linked Proteins" *Critical Reviews in Therapeutic Drug Carrier Systems* 9(3,4):249-304 (1992).

Ekwuribe et al. *Calcitonin Drug-Oligomer Conjugates, and Uses Thereof,* U.S. Appl. No. 10/166,355, filed Nov. 8, 2002, including Preliminary Amendment dated Feb. 26, 2003 and Supplemental Preliminary Amendment dated Mar. 31, 2003.

Ekwuribe et al. *Mixtures of Drug-Oligomer Conjugates Comprising Polyalkylene Glycol, Uses Thereof and Methods of Making Same,* U.S. Appl. No. 09/873,797, filed Jun. 4, 2001.

Ekwuribe, Nnochiri "Conjugation-Stabilized Polypeptide Compositions, Therapeutic Delivery and Diagnostic Formulations Comprising Same, and Method of Making and Using the Same" *Biotechnology Advances* 14(4):575-576 (1996) (Abstract).

Engel et al. "Insulin: Intestinal Absorption as Water-in-Oil-in-Water Emulsions" *Nature* 219:856-857 (1968).

Fasano, Alessio "Innovative strategies for the oral delivery of drugs and peptides" *TIBTECH* 16:152-157 (1998).

Forst et al. "New Aspects on Biological Activity of C-peptide in IDDM Patients" *Exp. Clin. Endocrinol. Diabetes* 106:270-276 (1998).

Gish et al. "Nucleic Acids. 11. Synthesis of 5'-Esters of 1-β-D-Arabinofuranosylcytosine Possessing Antileukemic and Immunosuppressive Activity" *J. Med. Chem.* 14(12):1159-1162 (1971).

Gombotz & Pettit "Biodegradable Polymers for Protein and Peptide Drug Delivery" *Bioconjugate Chem.* 6:332-351 (1995).

Hashimoto et al. "Synthesis of Palmitoyl Derivatives of Insulin and Their Biological Activities" *Pharmaceutical Research* 6(2):171-176 (1989).

Hinds et al. "Synthesis and Characterization of Poly(ethylene glycol)-Insulin Conjugates" *Bioconjugate Chem.* 11:195-201 (2000).

Hong et al. "Nucleoside Conjugates. 7. Synthesis and Antitumor Activity of 1-β-D-Arabinofuranosylcytosine Conjugates of Ether Lipids" *J. Med Chem.* 29:2038-2044 (1986).

Hostetler et al. "Synthesis and Antiretroviral Activity of Phospholipid Analogs of Azidothymidine and Other Antiviral Nucleosides" *The Journal of Biological Chemistry* 265(11):6112-6117 (1990).

Igarashi et al. "Biologically Active Peptides Conjugated with Lecithin for DDS" *Proceed. Intern. Symp. Cont. Rel. Bioactiv. Mater.* 17:367-368 (1990).

Kemmler et al. "On the Nature and Subcellular Localization of the Proinsulin Converting Enzymes" *Federation Proceedings* 30(Abstract 924):1210Abs (1971).

Kemmler et al. "Studies on the Conversion of Proinsulin to Insulin: I. Converison in Vitro with Trypsin and Carboxypeptidase B" *The Journal of Biological Chemistry* 246(22):6786-6791 (1971).

King et al. "Preparation of Protein Conjugates with Alkoxypolyethylene Glycols" *Int. J. Peptide Protein Res.* 16:147-155 (1980).

Kipnes et al. "Control of Postprandial Plasma Glucose by an Oral Insulin Product (HIM2) in Patients with Type 2 Diabetes" *Emerging Treatments and Technologies* 26:2 (2003).

Kipnes et al. "The Effects of an Oral Modified Insulin on Postprandial Blood Glucose Levels in Patients with Type 2 Diabetes Mellitus" American Diabetes Association Annual Meeting (Jun. 2001) (Poster).

Kipnes et al. "The Effects of an Oral Modified Insuling on Postprandial Blood Glucose Levels in Patients with Type 2 Diabetes" American Diabetes Association Annual Meeting (Jun. 24, 2001) (Abstract).

Kube, D.M. "Multitalented Proteins Play a Key Role in Therapeutics" *Genomics and Proteomics* (Sep. 2002).

Maislos et al. "The Source of the Circulating Aggregate of Insulin in Type I Diabetic Patients is Therapeutic Insulin" *J. Clin. Invest.* 77:717-723 (1986).

Savva & Huang "Effect of PEG Homopolymer and Grafted Amphiphilic PEG-Palmityl on the Thermotropic Phase Behavior of 1,2-Dipalmitoyl-SN-Glycero-3-Phosphocholine Bilayer" *Journal of Liposome Research* 9(3):357-365 (1999).

Marschutz et al. "Oral Peptide Drug Delivery: Polymer-Inhibitor Conjugates Protecting Insulin from Enzymatic Degradation In Vitro" *Biomaterials* 21:1499-1507 (2000).

Musabayane et al. "Orally Administered, Insulin-Loaded Amidated Pectin Hydrogel Beads Sustain Plasma Concentrations of Insulin in Streptozotocin-Diabetic Rats" *Journal of Endocrinology* 164:1-6 (2000).

Nucci et al. "The Therapeutic Value of Poly(ethylene Glycol)—Modified Proteins" *Ad. Drug. Del. Rev.* 6:133-151 (1991).

Oka et al. "Enhanced Intestinal Absorption of a Hydrophobic Polymer-Conjugated Protein Drug, Smancs, in an Oily Formulation" *Pharm. Res.* 7(8):852-855 (1990).

Pang, David C. "Bridging Gaps in Drug Discovery and Development" *Pharmaceutical Technology* 22:82-94 (Nov. 1998).

Patel et al. "Oral Administration of Insulin by Encapsulation Within Liposomes" *FEBS Lett.* 62(1):60-63 (1976).

Price, JC *Polyethlyene Glycol*, pp. 355-361.

Puskas et al. "Investigation of Chymotrypsin Digestion Profile of Orally Active Insulin Conjugate HIM2" *AAPS Pharm Sci.* 3(3) 2001 (Abstract).

Radhakrishnan et al. "Chemical Modification of Insulin with Amphiphilic Polymers Improves Intestinal Delivery," *Proceed. Intl. Symp. Control. Rel. Bioact. Mater.* 25:124-125(1998) (Abstract).

Radhakrishnan et al. "Oral Delivery of Insulin: Single Selective Modification at B29-LYS With Amphiphilic Oligomer" Program and Abstracts, 1999 National Meeting of the Ameri. Assoc. Pharm. Scient., New Orleans, LA (1999) (Abstract).

Radhakrishnan et al. "Structure-Activity Relationship of Insulin Modified with Amphiphilic Polymers" Program and Abstracts, 1998 National Meeting of the Amer. Assoc. Pharm. Scient., San Francisco, CA *Pharm. Sci.* 1(1):S-59 (1998) (Abstract).

Radhakrishnan et al. *Insulin Polypeptide-Oligomer Conjugates, Proinsulin Polypeptide-Oligomer Conjugates and Methods of Synthesizing Same*, U.S. Appl. No. 10/389,499, filed Mar. 17, 2003.

Ratner, R. E. et al. "Persistent Cutaneous Insulin Allergy Resulting from High-Molecular Weight Insulin Aggregates" *Diabetes* 39:728-733 (1990).

Richards et al. "Self-Association Properties of Monomeric Insulin Analogs Under Formulation Conditions" *Pharmaceutical Research* 15(9):1434-1441 (1998).

Robbins et al. "Antibodies to Covalent Aggregates of Insulin in Blood of Insulin-Using Diabetic Patients" *Diabetes* 36:838-841 (1987).

Russell-Jones, G. J. "Vitamin B12 Drug Delivery" *Proceed. Intern. Symp. Control. Rel. Bioactive. Mater.* 19:102-103 (1992).

Saffran et al. "A Model for the Study of the Oral Administration of Peptide Hormones" *Can J Biochem* 57:548-553 (1979).

Saffran, M. et al. "A New Approach to the Oral Administration of Insulin and Other Peptide Drugs" *Science* 233:1081-1084 (1986).

Santiago et al. "Oral Immunization of Rats with Influenza Virus M Protein (M1) Microspheres" *Proceed. Intern. Symp. Cont. Rel. Bioactive. Mater.* 19:116-117 (1992).

Shah and Shen "Transcellular Delivery of an Insulin-Transferrin Conjugate in Enterocyte-like Caco-2 Cells" *Journal of Pharmaceutical Sciences* 85(12):1306-1311 (1996).

Shichiri et al. "Enteral Absorption of Water-in-Oil-in-Water Insulin Emulsions in Rabbits" *Diabetologia* 10:317-321 (1974).

Soltero et al. *Insulin Polypeptide-Oligomer Conjugates, Proinsulin Polypeptide-Oligomer Conjugates and Methods of Synthesizing Same* U.S. Appl. No. 10/382,022, filed Mar. 5, 2003.

Soltero et al. *Pharmaceutical Compositions of Drug-Oligomer Conjugates and Methods of Treating Diseases Therewith* U.S. Appl. No. 10/382,069, filed Mar. 5, 2003.

Soltero et al. *Pharmaceutical Compositions of Insulin Drug-Oligomer Conjugates and Methods of Treating Diseases Therewith* U.S. Appl. No. 10/382,155, filed Mar. 5, 2003.

Still and McAllister "Effects of Orally Active Modified Insulin in Type 1 Diabetic Patients" *Clinical Pharmacol. Therap.* 69(2):P95 (Feb. 2001) (Abstract).

Still and McAllister "Effects of Orally Active Modified Insulin in Type I Diabetic Patients" Slide Presentation Annual Meeting of the American Society for Clinical Pharmacology & Therapeutics, Orlando, FL, Mar. 9, 2001.

Still and McAllister "Effects of Orally Active Modified Insulin in Type I Diabetic Patients" Annual Meeting of the American Society for Clinical Pharmacology & Therapeutics, Orlando, FL, Mar. 9, 2001 (Handout).

Still et al. "Magnitude and Variability of Pharmacokinetic and Glucodynamic Responses to Modified Human Insulin Administered Orally to Healthy Volunteers" *Diabetes Research and Clinical Practice* 56:S77 (2002).

Still et al. *Methods of Reducing Hypoglycemic Episodes in the Treatment of Diabetes Mellitus*, U.S. Appl. No. 10/461,199, filed Jun. 13, 2003.

Still, J. Gordon "Development of Oral Insulin: Progress and Current Status" *Diabetes/Metabolism Research and Reviews* 18(1):S29-S37 (2002).

Still, J. Gordon "Oral Insulin Development" Slide Presentation, VI International St. Barts Symposium Diabetes 2000: Therapy and Technology, London, England, May 12, 2000.

Szleifer et al. "Spontaneous Liposome Formation Induced by Grafted Poly(Ethylene Oxide) Layers: Theoretical Prediction and Experimental Verification" *Proceedings of the National Academy of Sciences of the United States of America* 95(3):1032-1037 (1998).

Taniguchi et al. "Synthesis of Acyloyl Lysozyme and Improvement of its Lymphatic Transport Following Small Intestinal Administration in Rats" *Proceed. Intern. Symp. Control. Rel. Bioactiv. Mater.* 19:104-105 (1992).

Uchio et al. "Site-Specific Insulin Conjugates with Enhanced Stability and Extended Action Profile" *Advanced Drug Delivery Reviews* 35:289-306 (1999).

Vreeland et al. "Molar Mass Profiling of Synthetic Polymers by Free-Solution Capillary Electrophoresis of DNA-Polymer Conjugates" *Analytical Chemistry* 73(8):1795-1803 (2001).

Wahren et al. "Role of C-peptide in Human Physiology" *Am. J. Physiol. Endocrinol. Metab.* 278:E759-E768 (2000).

Zalipsky et al. "Attachment of Drugs to Polyethylene Glycols" *Eur. Polym. J.* 19(12):1177-1183 (1983).

Ziv and Bendayan "Intestinal Absorption of Peptides Through the Enterocytes" *Microscopy Research and Technique* 49:346-352 (2000).

Mehvar, Reza; Modulation of the Pharmacokinetics and Pharmacodynamics of Proteins by Polyethylene Glycol Conjugation; *J. Pharm. Pharmaceut Sci.*; 3(1):125-136; 2000.

Larry J. Suva et al.; Design, Synthesis and Utility of Novel Benzophenone-Containing Calcitonin Analogs for Photoaffinity Labeling the Calcitonin Receptor; The Journal of Pharmacology and Experimental Therapeutics; 1997; vol. 283, No. 2; pp. 876-884; The American Society for Pharmacology and Experimental Therapeutics.

Kang Choon Lee et al.; Isolation, Characterization, and Stability of Positional Isomers of Mono-PEGylated Salmon Calcitonins; Pharmaceutical Research; 1999; vol. 16, No. 6, pp. 813-818; Plenum Publishing Corporation.

Haeshin Lee et al.; Preparation and Characterization of Mono-PEGylated Epidermal Growth Factor: Evaluation of In Vitro Biologic Activity; Pharmaceutical Research; 2002; vol. 19, No. 6, pp. 845-851; Plenum Publishing Corporation.

Andrea Lucke et al.; Biodegradable poly(D,L-lactic acid)-poly(ethylene glycol)-monomethyl ether diblock copolymers: structures and surface properties relevant to their use as biomaterials; Biomaterials; 2000; 21, pp. 2361-2370; Elsevier Science Ltd.

Jong-Hoon Lee et al.; Polymeric nanoparticle composed of fatty acids and poly(ethylene glycol) as a drug carrier; International Journal of Pharmaceutics; 2003; 251, pp. 23-32; Elsevier Science B.V.

Samuel Zalipsky; Synthesis of an End-Group Functionalized Polyethylene Glycol-Lipid Conjugate for Preparation of Polymer-Grafted Liposomes; Bioconjugate Chemistry; 1993; No. 4, pp. 296-299; American Chemical Society.

Muneaki Hashimoto et al.; Synthesis of Palmitoyl Derivatives of Insulin and Their Biological Activities; Pharmaceutical Research; 1989; vol. 6, No. 2, pp. 171-176; Plenum Publishing Corporation.

Christopher H. Price et al.; Molecular Drug Delivery: Drug-Polymer Conjugates for Delivery and Targeting; Abstracts of Papers American Chemical Society; (2000); vol. 219, No. 1-2, pp. MEDI 178; San Francisco, CA, USA.

A.J. Higgins et al.; Enhanced Bioefficacy of a Novel Orally Active Calcitonin Analog; British Journal of Pharmacology; (2001); vol. 134, No. Proceedings Supplement, p. 53P; Dublin, Ireland.

* cited by examiner

CALCITONIN DRUG-OLIGOMER CONJUGATES, AND USES THEREOF

CROSSREFERENCE TO RELATED APPLICATION

This application is a Continuation in Part of and claims priority to U.S. application Ser. No. 09/873,777, filed on Jun. 4, 2001, now U.S. Pat. No. 6,713,452, which is incorporated by reference herein in its entirely.

FIELD OF THE INVENTION

The present invention relates to drug-oligomer conjugates, and, more particularly, to calcitonin drug-oligomer conjugates.

BACKGROUND OF THE INVENTION

Calcitonin is a naturally occurring hormone with a short half-life that is believed to act directly on osteoclasts (via receptors on the cell surface for calcitonin). This action may directly inhibit osteoclastic bone resorption, which may lead to hypocalcemic and/or hypophosphatemic serum effects. Calcitonin may be useful in treating various bone disorders including, but not limited to, osteoporosis and Paget's disease.

Osteoporosis is a bone disease in which bone tissue is normally mineralized, but the amount of bone is decreased and the structural integrity of trabecular bone is impaired. Cortical bone becomes more porous and thinner. This makes the bone weaker and more likely to fracture. In the United States, about 21% of postmenopausal women have osteoporosis (low bone density), and about 16% have had a fracture. In women older than 80, about 40% have experienced a fracture of the hip, vertebra, arm, or pelvis. The population of older men and women has been increasing, and therefore the number of people with osteoporosis is increasing.

Calcitonin given as a subcutaneous injection has shown significant improvements in bone density; however, a high incidence of side effects, including pain at the injection site, flushing and nausea, have been reported which may limit the use of the drug.

Paget's disease of bone is a metabolic bone disorder of unknown origin which normally affects older people. The disease causes an increased and irregular formation of bone as the bone cells, which are responsible for dissolving the body's old bone and replacing it with new, become out of control. Over a period of time the deformed new bone becomes larger, weaker and has more blood vessels than normal bone. Unlike normal bone, the structure is irregular and consequently weaker, which makes it prone to fracture even after a minor injury.

In its mildest form the disease has no symptoms. In more severe cases the pain can be intense. The relentless progression of the disease may cause bones to bow, the skull may increase in size and the spinal column may curve. As the bones enlarge they may cause pressure on nearby nerves which can result in muscle weakness. In the case of severe skull enlargement this pressure can result in deafness, disturbed vision, dizziness and tinnitus.

Calcitonin may be effective in treating disorders of increased skeletal remodeling, such as Paget's disease. In treating Paget's disease, chronic use of calcitonin may produce long-term reduction in symptoms; however, side effects of calcitonin administration may include nausea, hand swelling, urticaria, and intestinal cramping.

Various references have proposed conjugating polypeptides such as calcitonin with polydispersed polyethylene glycol or polyethylene glycol-containing polymers. For example, U.S. Pat. No. 5,359,030 to Ekwuribe proposes various genera of polypeptides such as calcitonin conjugated with polydispersed mixtures of polyethylene glycol modified glycolipid polymers and polydispersed mixtures of polyethylene glycol modified fatty acid polymers.

It is desirable to provide additional calcitonin drug-oligomer conjugates.

SUMMARY OF THE INVENTION

Calcitonin drug-oligomer conjugates according to embodiments of the present invention may lower serum calcium levels by 10, 15 or even 20 percent or more. Moreover, calcitonin drug-oligomer conjugates according to embodiments of the present invention may be more effective at surviving an in vitro model of intestinal digestion than non-conjugated calcitonin. Furthermore, calcitonin drug-oligomer conjugates according to embodiments of the present invention may exhibit a higher bioavailability than non-conjugated calcitonin.

According to embodiments of the present invention, a calcitonin drug-oligomer conjugate including a calcitonin drug coupled to an oligomer that includes a single polyalkylene glycol moiety consisting of between 4 and 10 polyalkylene glycol subunits is provided.

According to other embodiments of the present invention, a calcitonin drug-oligomer conjugate is provided that includes the structure of Formula I:

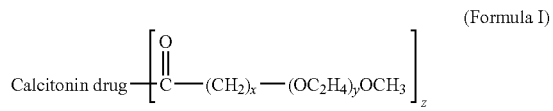

(Formula I)

wherein
  x is an integer from 5 to 9;
  y is an integer from 4 to 10; and
  z is an integer from 1 to the number of conjugation sites on the calcitonin drug.

According to still other embodiments of the present invention, a calcitonin drug-oligomer conjugate is provided that includes the structure of Formula II:

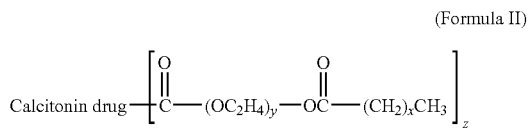

(Formula II)

wherein
  x is an integer from 12 to 18;
  y is an integer from 4 to 10; and
  z is an integer from 1 to the number of conjugation sites on the calcitonin drug.

Pharmaceutical compositions that include conjugates of the present invention as well as methods of treating bone disorders in a subject in need of such treatment by administering an effective amount of such conjugates are also provided.

Calcitonin drug-oligomer conjugates according to embodiments of the present invention may lower serum calcium levels by 20 percent or more. Moreover, such conjugates may provide decreased degradation by intestinal enzymes and/or provide increased bioavailability when compared to non-conjugated calcitonin.

DETAILED DESCRIPTION OF PREFERRED EMBODIMENTS

Figure 1:
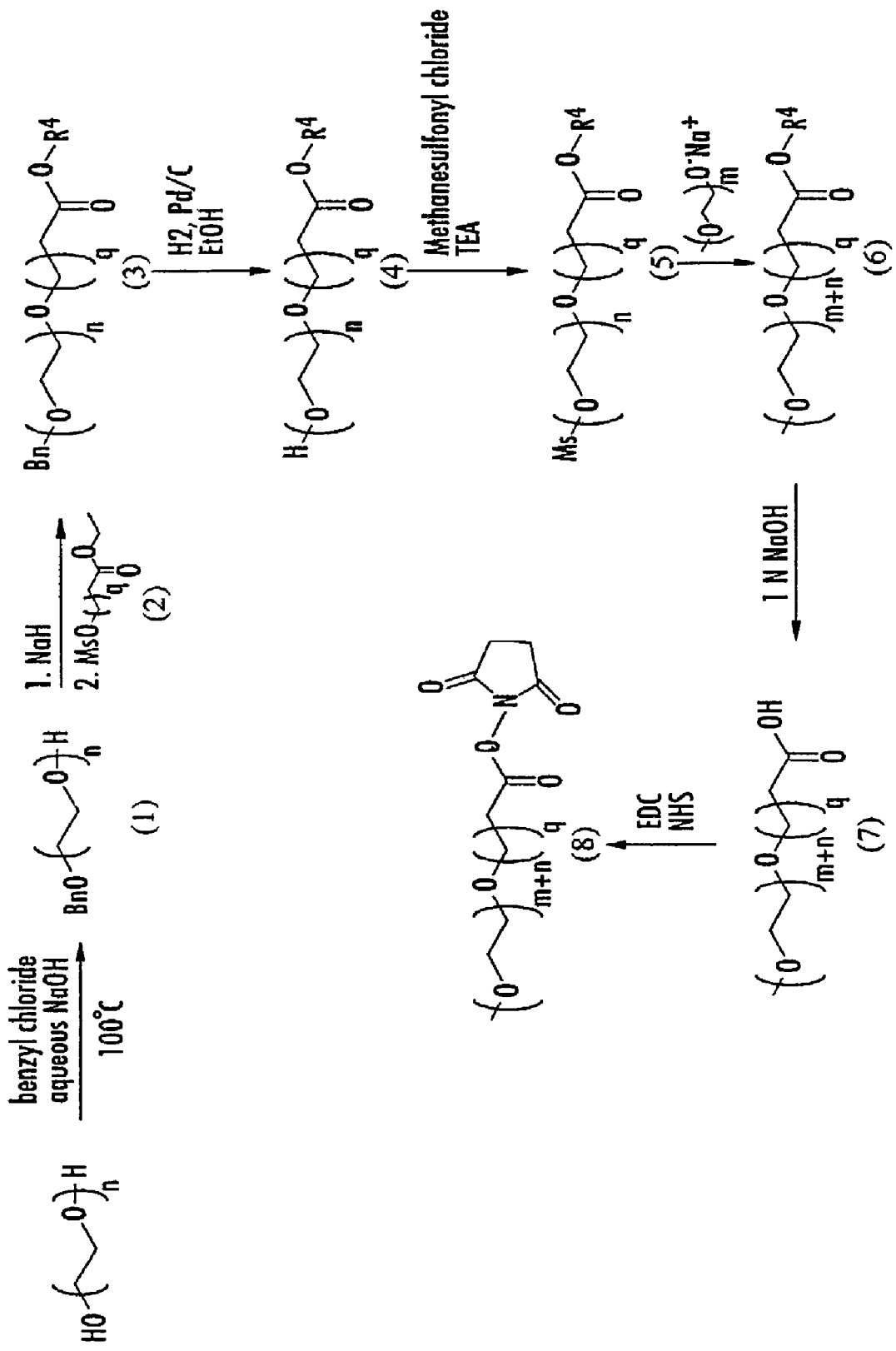
FIG. 1 illustrates a generic scheme for synthesizing a mixture of activated polymers comprising a polyethylene glycol moiety and a fatty acid moiety according to embodiments of the present invention.

The invention will now be described with respect to preferred embodiments described herein. It should be appreciated however that these embodiments are for the purpose of illustrating the invention, and are not to be construed as limiting the scope of the invention as defined by the claims.

As used herein, the term "non-polydispersed" is used to describe a mixture of compounds having a dispersity that is in contrast to the polydispersed mixtures described in U.S. Pat. No. 5,359,030 to Ekwuribe.

As used herein, the term "substantially monodispersed" is used to describe a mixture of compounds wherein at least about 95 percent of the compounds in the mixture have the same molecular weight.

As used herein, the term "monodispersed" is used to describe a mixture of compounds wherein about 100 percent of the compounds in the mixture have the same molecular weight.

As used herein, the term "substantially purely monodispersed" is used to describe a mixture of compounds wherein at least about 95 percent of the compounds in the mixture have the same molecular weight and have the same molecular structure. Thus, a substantially purely monodispersed mixture is a substantially monodispersed mixture, but a substantially monodispersed mixture is not necessarily a substantially purely monodispersed mixture.

As used herein, the term "purely monodispersed" is used to describe a mixture of compounds wherein about 100 percent of the compounds in the mixture have the same molecular weight and have the same molecular structure. Thus, a purely monodispersed mixture is a monodispersed mixture, but a monodispersed mixture is not necessarily a purely monodispersed mixture.

As used herein, the term "weight average molecular weight" is defined as the sum of the products of the weight fraction for a given molecule in the mixture times the mass of the molecule for each molecule in the mixture. The "weight average molecular weight" is represented by the symbol $M_w$.

As used herein, the term "number average molecular weight" is defined as the total weight of a mixture divided by the number of molecules in the mixture and is represented by the symbol $M_n$.

As used herein, the term "dispersity coefficient" (DC) is defined by the formula:

$$DC = \frac{\left(\sum_{i=1}^{n} N_i M_i\right)^2}{\sum_{i=1}^{n} N_i M_i^2 \sum_{i=1}^{n} N_i - \left(\sum_{i=1}^{n} N_i M_i\right)^2}$$

wherein:
n is the number of different molecules in the sample;
$N_i$ is the number of $i^{th}$ molecules in the sample; and
$M_i$ is the mass of the $i^{th}$ molecule.

As used herein, the term "intra-subject variability" means the variability in activity occurring within the same subject when the subject is administered the same dose of a drug or pharmaceutical composition at different times.

As used herein, the term "inter-subject variability" means the variability in activity between two or more subjects when each subject is administered the same dose of a given drug or pharmaceutical formulation.

As used herein, the term "bioefficacy" means the ability of a drug or drug conjugate to interact with one or more desired receptors in vivo.

As used herein, the term "calcitonin drug" means a drug possessing all or some of the biological activity of calcitonin.

As used herein, the term "calcitonin" means chicken calcitonin, eel calcitonin, human calcitonin, porcine calcitonin, rat calcitonin, salmon calcitonin, or the like provided by natural, synthetic, or genetically engineered sources.

As used herein, the term "calcitonin analog" means calcitonin wherein one or more of the amino acids have been replaced while retaining some or all of the activity of the calcitonin. The analog is described by noting the replacement amino acids with the position of the replacement as a superscript followed by a description of the calcitonin. For example, "$Pro^2$ calcitonin, human" means that the glycine typically found at the 2 position of a human calcitonin molecule has been replaced with proline.

Calcitonin analogs may be obtained by various means, as will be understood by those skilled in the art. For example, certain amino acids may be substituted for other amino acids in the calcitonin structure without appreciable loss of interactive binding capacity with structures such as, for example, antigen-binding regions of antibodies or binding sites on substrate molecules. As the interactive capacity and nature of calcitonin defines its biological functional activity, certain amino acid sequence substitutions can be made in the amino acid sequence and nevertheless remain a polypeptide with like properties.

In making such substitutions, the hydropathic index of amino acids may be considered. The importance of the hydropathic amino acid index in conferring interactive biologic function on a polypeptide is generally understood in the art. It is accepted that the relative hydropathic character of the amino acid contributes to the secondary structure of the resultant polypeptide, which in turn defines the interaction of the polypeptide with other molecules, for example, enzymes, substrates, receptors, DNA, antibodies, antigens, and the like. Each amino acid has been assigned a hydropathic index on the basis of its hydrophobicity and charge characteristics as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). As will be understood by those skilled in the art, certain amino acids may be substituted by other amino acids having a similar hydropathic index or score and still result in a polypeptide with similar biological activity, i.e., still obtain a biological functionally equivalent polypeptide. In making such changes, the substitution of amino acids whose hydropathic indices are within ±2 of each other is preferred, those which are within ±1 of each other are particularly preferred, and those within ±0.5 of each other are even more particularly preferred.

It is also understood in the art that the substitution of like amino acids can be made effectively on the basis of hydrophilicity. U.S. Pat. No. 4,554,101 provides that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (±3.0); aspartate (+3.0±1); glutamate (+3.0±1); seine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). As is understood by those skilled in the art, an amino acid can be substituted for another having a similar hydrophilicity value and still obtain a biologically equivalent, and in particular, an immunologically equivalent polypeptide. In such changes, the substitution of amino acids whose hydrophilicity values are within ±2 of each other is preferred, those which are within ±1 of each other are particularly preferred, and those within ±0.5 of each other are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions (i.e., amino acids that may be interchanged without significantly altering the biological activity of the polypeptide) that take various of the foregoing characteristics into consideration are well known to those of skill in the art and include, for example: arginine and lysine; glutamate and aspartate; serine and threonine; glutamine and asparagine; and valine, leucine and isoleucine.

As used herein, the term "calcitonin fragment" means a segment of the amino acid sequence found in the calcitonin that retains some or all of the activity of the calcitonin.

As used herein, the term "calcitonin fragment analog" means a segment of the amino acid sequence found in the calcitonin molecule wherein one or more of the amino acids in the segment have been replaced while retaining some or all of the activity of the calcitonin.

As used herein, the term "PEG" refers to straight or branched polyethylene glycol polymers, and includes the monomethylether of polyethylene glycol (mPEG). The terms "PEG subunit" and polyethylene glycol subunit refer to a single polyethylene glycol unit, i.e.,

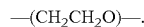

—(CH$_2$CH$_2$O)—.

As used herein, the term "lipophilic" means the ability to dissolve in lipids and/or the ability to penetrate, interact with and/or traverse biological membranes, and the term, "lipophilic moiety" or "lipophile" means a moiety which is lipophilic and/or which, when attached to another chemical entity, increases the lipophilicity of such chemical entity. Examples of lipophilic moieties include, but are not limited to, alkyls, fatty acids, esters of fatty acids, cholesteryl, adamantyl and the like.

As used herein, the term "lower alkyl" refers to substituted or unsubstituted alkyl moieties having from 1 to 5 carbon atoms.

As used herein, the term "higher alkyl" refers to substituted or unsubstituted alkyl moieties having 6 or more carbon atoms.

In embodiments of the present invention, a calcitonin drug-oligomer conjugate comprises a calcitonin drug coupled to an oligomer that comprises a single polyalkylene glycol moiety consisting of from 4 to 10 polyalkylene glycol subunits.

The calcitonin drug is preferably calcitonin. More preferably, the calcitonin drug is salmon calcitonin. However, it is to be understood that the calcitonin drug may be selected from various calcitonin drugs known to those skilled in the art including, for example, calcitonin precursor peptides, calcitonin, calcitonin analogs, calcitonin fragments, and calcitonin fragment analogs. Calcitonin precursor peptides include, but are not limited to, katacalcin (PDN-21) (C-procalcitonin), and N-proCT (amino-terminal procalcitonin cleavage peptide), human. Calcitonin analogs may be provided by substitution of one or more amino acids in calcitonin as described above. Calcitonin fragments include, but are not limited to, calcitonin 1-7, human; and calcitonin 8-32, salmon. Calcitonin fragment analogs may be provided by substitution of one or more of the amino acids in a calcitonin fragment as described above.

The oligomer may be various oligomers comprising a single polyalkylene glycol moiety consisting of from 4 to 10 polyalkylene glycol subunits as will be understood by those skilled in the art. In various embodiments, the oligomers comprise a single polyalkylene glycol moiety consisting of from a lower limit of 4, 5, 6, 7, 8, or 9 polyalkylene glycol moieties to an upper limit of 5, 6, 7, 8, 9, or 10 polyalkylene glycol moieties.

The polyalkylene glycol moiety is preferably a poly(loweralkylene glycol) moiety such as polyethylene glycol, polypropylene glycol, or polybutylene glycol. In particular embodiments, the polyalkylene glycol moiety is polyethylene glycol.

In addition to the polyalkylene glycol moiety, the oligomer may comprise one or more other moieties as will be understood by those skilled in the art including, but not limited to, additional hydrophilic moieties, lipophilic moieties, spacer moieties, linker moieties, salt-forming moieties, and terminating moieties. The various moieties in the oligomer are covalently coupled to one another by either hydrolyzable or non-hydrolyzable bonds.

In addition to the polyalkylene glycol moiety, the oligomer may further comprise one or more additional hydrophilic moieties (i.e., moieties in addition to the polyalkylene glycol moiety) including, but not limited to, sugars. Preferably, oligomers according to embodiments of the present invention comprise the single polyethylene glycol moiety and no additional hydrophilic moieties.

In addition to the polyalkylene glycol moiety, the oligomer preferably further comprises one or more lipophilic moieties as will be understood by those skilled in the art. The lipophilic moiety has at least 1, 2, 3, 4, 5, or 6 carbon atoms. The lipophilic moiety preferably has between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30 carbon atoms. The lipophilic moiety more preferably has between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or carbon atoms. The lipophilic moiety even more preferably has between a lower limit of 3, 4, 5, 6, 7, 8, or 9 and an upper limit of 4, 5, 6, 7, 8, 9, 10, 11, 12, 13, or 14 carbon atoms. The lipophilic moiety still more preferably has between a lower limit of 3, 4, 5, 6, or 7 and an upper limit of 6, 7, 8, 9, or 10 carbon atoms. The lipophilic moiety is preferably selected from the group consisting of saturated or unsaturated, linear or branched alkyl moieties, saturated or unsaturated, linear or branched fatty acid moieties, cholesterol, and adamantane. Exemplary alkyl moieties include, but are not limited to, saturated, linear alkyl moieties such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl; saturated, branched alkyl moieties such as isopropyl, sec-butyl, tert-butyl, 2-methylbutyl, tert-pentyl, 2-methyl-pentyl, 3-methylpentyl, 2-ethylhexyl, 2-propylpentyl; and unsaturated alkyl moieties derived from the above saturated alkyl moieties including, but not limited to, vinyl, allyl, 1-butenyl, 2-butenyl, ethynyl, 1-propynyl, and 2-propynyl. Exemplary fatty acid moieties include, but are not limited to, unsaturated fatty acid moieties such as lauroleate, myristoleate, palmitoleate, oleate, elaidate, erucate, linoleate, linolenate, arachidonate, eicosapentaentoate, and docosahexaenoate; and saturated fatty acid moieties such as acetate, caproate, caprylate, caprate, laurate, arachidate, behenate, lignocerate, and cerotate.

In addition to the polyalkylene glycol moiety, the oligomer may further comprise one or more spacer moieties as will be understood by those skilled in the art. Spacer moieties may, for example, be used to separate a the polyalkylene glycol moiety from a lipophilic moiety, to separate a lipophilic moiety or polyalkylene glycol moiety from the calcitonin drug, or to separate the polyalkylene glycol moiety or lipophilic moiety from a linker moiety, for example. Spacer moieties are preferably selected from the group consisting of sugar, cholesterol and glycerine moieties. Sugar moieties may be various sugar moieties as will be understood by those skilled in the art including, but not limited to, monosaccharide moieties and disaccharide moieties. Preferred monosaccharide moieties have between 4 and 6 carbon atoms.

In addition to the polyalkylene glycol moiety, the oligomer may further comprise one or more linker moieties that are used to couple the oligomer with the calcitonin drug as will be understood by those skilled in the art. Linker moieties are preferably selected from the group consisting of alkyl and fatty acid moieties. The alkyl linker moiety may be a saturated or unsaturated, linear or branched alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety may be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The alkyl linker moiety may have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms, and preferably has between 1, 2, 3, 4, or 5 and 8, 9, 10, 11, or 12 carbon atoms. The fatty acid linker moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate. The fatty acid linker moiety may have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms and preferably has between 1, 2, 3, 4, or 5 and 8, 10, 12, 14 or 16 carbon atoms.

In addition to the polyalkylene glycol moiety, the oligomer may further comprise a salt-forming moiety such as an ammonium moiety or a carboxylate moiety.

In addition to the polyalkylene glycol moiety, the oligomer may further comprise one or more terminating moieties at the one or more ends of the oligomer, which are not coupled to the calcitonin drug. The terminating moiety is preferably an alkyl or alkoxy moiety. The alkyl or alkoxy moiety preferably has between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms. The alkyl or alkoxy moiety more preferably has between a lower limit of 1, 2, 3, 4, 5, 6, or 7 and an upper limit of 5, 6, 7, 8, 9, 10, 11, 12, 13, or 14 carbon atoms. The alkyl or alkoxy moiety even more preferably has between a lower limit of 1, 2, 3, 4, or 5 and an upper limit of 5, 6, 7, 8, 9, or 10 carbon atoms. The alkyl or alkoxy moiety still more preferably has between a lower limit of 1, 2, 3, or 4 and an upper limit of 5, 6, or 7 carbon atoms. The alkyl moiety may be a linear or branched, saturated or unsaturated alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety may be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The terminating moiety is more preferably a lower alkyl moiety such as methyl, ethyl, propyl, isopropyl, butyl, sec-butyl, tert-butyl, pentyl, or tert-pentyl, or a lower alkoxy moiety such as methoxy, ethoxy, propoxy, isopropoxy, butoxy, sec-butoxy, tert-butoxy, pentyloxy, or tert-pentyloxy. Most preferably, the terminating moiety is methyl or methoxy. While the terminating moiety is preferably an alkyl or alkoxy moiety, it is to be understood that the terminating moiety may be various moieties as will be understood by those skilled in the art including, but not limited to, sugars, cholesterol, alcohols, and fatty acids.

The oligomer is preferably covalently coupled to the calcitonin drug. In some embodiments, the calcitonin drug is coupled to the oligomer utilizing a hydrolyzable bond (e.g., an ester or carbonate bond). A hydrolyzable coupling may provide a calcitonin drug-oligomer conjugate that acts as a prodrug. In certain instances, for example where the calcitonin drug-oligomer conjugate is inactive (i.e., the conjugate lacks the ability to affect the body through the calcitonin drug's primary mechanism of action), a hydrolyzable coupling may provide for a time-release or controlled-release effect, administering the calcitonin drug over a given time period as one or more oligomers are cleaved from their respective calcitonin drug-oligomer conjugates to provide the active drug. In other embodiments, the calcitonin drug is coupled to the oligomer utilizing a non-hydrolyzable bond (e.g., a carbamate, amide, or ether bond). Use of a non-hydrolyzable bond may be preferable when it is desirable to allow the calcitonin drug-oligomer conjugate to circulate in the bloodstream for an extended period of time, preferably at least 2 hours. When the oligomer is covalently coupled to the calcitonin drug, the oligomer further comprises one or more bonding moieties that are used to covalently couple the oligomer with the calcitonin drug as will be understood by those skilled in the art. Bonding moieties are preferably selected from the group consisting of covalent bond(s), ester moieties, carbonate moieties, carbamate moieties, amide moieties and secondary amine moieties. More than one moiety on the oligomer may be covalently coupled to the calcitonin drug.

While the oligomer is preferably covalently coupled to the calcitonin drug, it is to be understood that the oligomer may be non-covalently coupled to the calcitonin drug to form a non-covalently conjugated calcitonin drug-oligomer complex. As will be understood by those skilled in the art, non-covalent couplings include, but are not limited to, hydrogen bonding, ionic bonding, Van der Waals bonding, and micellular or liposomal encapsulation. According to embodiments of the present invention, oligomers may be suitably constructed, modified and/or appropriately functionalized to impart the ability for non-covalent conjugation in a selected manner (e.g., to impart hydrogen bonding capability), as will be understood by those skilled in the art. According to other embodiments of present invention, oligomers may be derivatized with various compounds including, but not limited to, amino acids, oligopeptides, peptides, bile acids, bile acid derivatives, fatty acids, fatty acid derivatives, salicylic acids, salicylic acid derivatives, aminosalicylic acids, and aminosalicylic acid derivatives. The resulting oligomers can non-covalently couple (complex) with drug molecules, pharmaceutical products, and/or pharmaceutical excipients. The resulting complexes preferably have balanced lipophilic and hydrophilic properties. According to still other embodiments of the present invention, oligomers may be derivatized with amine and/or alkyl amines. Under suitable acidic conditions, the resulting oligomers can form non-covalently conjugated complexes with drug molecules, pharmaceutical products and/or pharmaceutical excipients. The products resulting from such complexation preferably have balanced lipophilic and hydrophilic properties.

More than one oligomer (i.e., a plurality of oligomers) may be coupled to the calcitonin drug. The oligomers in the plurality are preferably the same. However, it is to be understood that the oligomers in the plurality may be different from one another, or, alternatively, some of the oligomers in the plurality may be the same and some may be different. When a plurality of oligomers are coupled to the calcitonin drug, it may be preferable to couple one or more of the oligomers to the calcitonin drug with hydrolyzable bonds and couple one or more of the oligomers to the calcitonin drug with non-hydrolyzable bonds. Alternatively, all of the bonds coupling the plurality of oligomers to the calcitonin drug may be hydrolyzable, but have varying degrees of hydrolyzability such that, for example, one or more of the oligomers is rapidly removed from the calcitonin drug by hydrolysis in the body and one or more of the oligomers is slowly removed from the calcitonin drug by hydrolysis in the body.

The oligomer may be coupled to the calcitonin drug at various nucleophilic residues of the calcitonin drug including, but not limited to, nucleophilic hydroxyl functions and/or amino functions. When the calcitonin drug is a polypeptide, a nucleophilic hydroxyl function may be found, for example, at serine and/or tyrosine residues, and a nucleophilic amino function may be found, for example, at histidine and/or lysine residues, and/or at the one or more N-termini of the polypeptide. When an oligomer is coupled to the one or more N-terminus of the calcitonin polypeptide, the coupling preferably forms a secondary amine. When the calcitonin drug is salmon calcitonin, for example, the oligomer may be coupled to an amino functionality of the salmon calcitonin, including the amino functionality of $Lys^{11}$, $Lys^{18}$ and/or the N-terminus. While one or more oligomers may be coupled to the salmon calcitonin, a higher bioefficacy, such as improved serum calcium lowering ability, is observed for the di-conjugated salmon calcitonin where an oligomer is coupled to the amino functionalities of $Lys^{11}$ and the $Lys^{18}$.

In other embodiments according to the present invention, the calcitonin drug-oligomer conjugate comprises the structure of Formula I:

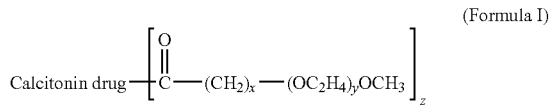

(Formula I)

wherein the calcitonin drug is a calcitonin drug as described above and the oligomer, which is shown in the brackets of Formula I, is covalently coupled to the calcitonin drug at any of the various conjugation sites on the calcitonin drug;

x is an integer from a lower limit of 5, 6, 7, or 8 to an upper limit of 6, 7, 8, or 9, and is preferably 7;

y is an integer from a lower limit of 4, 5, 6, 7, 8, or 9 to an upper limit of 5, 6, 7, 8, 9, or 10, and is preferably 7; and z is an integer from 1 to the number of conjugation sites on the calcitonin drug. In some embodiments, z is preferably 1 or 2, and is more preferably 2.

In preferred embodiments, the calcitonin drug is salmon calcitonin and z is 1, with the oligomer being covalently coupled to the amine function at Lys$^{11}$ or Lys$^{18}$ of the salmon calcitonin. In more preferred embodiments, the calcitonin drug is salmon calcitonin and z is 2, with one oligomer being covalently coupled to the amine function at Lys$^{11}$ of the salmon calcitonin and the other oligomer being covalently coupled to the amine function at Lys$^{18}$ of the salmon calcitonin.

According to still other embodiments of the present invention, the calcitonin drug-oligomer conjugate comprises the structure of Formula II:

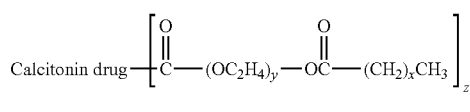

(Formula II)

wherein
the calcitonin drug is a calcitonin drug as described above and the oligomer, which is shown in the brackets of Formula II, is covalently coupled to the calcitonin drug at any of the various conjugation sites on the calcitonin drug;

x is an integer from a lower limit of 12, 13, 14, 15, 16 or 17 to an upper limit of 13, 14, 15, 16, 17, or 18, and is preferably 16;

y is an integer from a lower limit of 4, 5, 6, 7, 8, or 9 to an upper limit of 5, 6, 7, 8, 9, or 10, and is preferably 8; and z is an integer from 1 to the number of conjugation sites on the calcitonin drug. In some embodiments, z is preferably 1 or 2, and is more preferably 2.

In preferred embodiments, the calcitonin drug is salmon calcitonin and z is 1, with the oligomer being covalently coupled to the amine function at Lys$^{11}$ or Lys$^{18}$ of the salmon calcitonin. In more preferred embodiments, the calcitonin drug is salmon calcitonin and z is 2, with one oligomer being covalently coupled to the amine function at Lys$^{11}$ of the salmon calcitonin and the other oligomer being covalently coupled to the amine function at Lys$^{18}$ of the salmon calcitonin.

In some embodiments of the present invention, the calcitonin drug-oligomer conjugates are polydispersed. Polydispersed calcitonin drug-oligomer conjugates may be synthesized by various means as will be understood by those skilled in the art. For example, the synthesis routes described below for non-polydispersed conjugates can be performed using polydispersed polyalkylene glycol to provide polydispersed calcitonin drug-oligomer conjugates.

In other embodiments, the calcitonin drug-oligomer conjugates are non-polydispersed. Non-polydispersed conjugates may have varying degrees of polydispersity and still be considered non-polydispersed. For example, in some embodiments, the non-polydispersed calcitonin drug-oligomer conjugates are substantially monodispersed. In other embodiments, the non-polydispersed calcitonin drug-oligomer conjugates are substantially purely monodispersed. In still other embodiments, the non-polydispersed calcitonin drug-oligomer conjugates are monodispersed. In yet other embodiments, the non-polydispersed calcitonin drug-oligomer conjugates are purely monodispersed.

In other embodiments, the non-polydispersed calcitonin drug-oligomer conjugates have a molecular weight distribution with a standard deviation of less than about 22 Daltons.

The standard deviation is preferably less than about 14 Daltons and is more preferably less than about 11 Daltons. The molecular weight distribution may be determined by methods known to those skilled in the art including, but not limited to, size exclusion chromatography such as gel permeation chromatography as described, for example, in H. R. Allcock & F. W. Lampe, CONTEMPORARY POLYMER CHEMISTRY 394-402 (2d. ed., 1991). The standard deviation of the molecular weight distribution may then be determined by statistical methods as will be understood by those skilled in the art.

In still other embodiments, the non-polydispersed calcitonin drug-oligomer conjugates have a dispersity coefficient (DC) greater than 10,000 where $$DC = \frac{\left(\sum_{i=1}^{n} N_i M_i\right)^2}{\sum_{i=1}^{n} N_i M_i^2 \sum_{i=1}^{n} N_i - \left(\sum_{i=1}^{n} N_i M_i\right)^2}$$

wherein:
n is the number of different molecules in the sample;
$N_i$ is the number of $i^{th}$ molecules in the sample; and
$M_i$ is the mass of the $i^{th}$ molecule.

The non-polydispersed conjugates preferably have a dispersity coefficient greater than 100,000. More preferably, the dispersity coefficient of the conjugates is greater than 500,000 and, most preferably, the dispersity coefficient is greater than 10,000,000. The variables n, $N_i$, and $M_i$ may be determined by various methods as will be understood by those skilled in the art, including, but not limited to, methods described below in Example 34.

Non-polydispersed calcitonin drug-oligomer conjugates according to the present invention may be synthesized by methods described in U.S. patent application Ser. No. 09/873,777 entitled "Mixtures of Calcitonin Drug-Oligomer Conjugates Comprising Polyalkylene Glycol, Uses Thereof, and Methods of Making Same," the disclosure of which is incorporated herein by reference in its entirety. In general, a non-polydispersed oligomer is prepared by synthesizing a non-polydispersed polyalkylene containing oligomer by a method such as that illustrated in FIG. 1, which will now be described. The synthesis of non-polydispersed polyethylene glycol-containing oligomers begins by the preparation of the monobenzyl ether (1) of a non-polydispersed polyethylene glycol. An excess of a commercially available non-polydispersed polyethylene glycol is reacted with benzyl chloride in the presence of aqueous sodium hydroxide as described by Coudert et al (*Synthetic Communications,* 16(1): 19-26 (1986)). The sodium salt of 1 is then prepared by the addition of NaH, and this sodium salt is allowed to react with the mesylate synthesized from the ester of a hydroxyalkanoic acid (2). The product (3) of the displacement of the mesylate is debenzylated via catalytic hydrogenation to obtain the alcohol (4). The mesylate (5) of this alcohol may be prepared by addition of methanesulfonyl chloride and used as the electrophile in the reaction with the sodium salt of the monomethyl ether of a non-polydispersed polyethylene glycol derivative, thereby extending the polyethylene glycol portion of the oligomer to the desired length, obtaining the elongated ester (6). The ester may be hydrolyzed to the acid (7) in aqueous base and transformed into the activated ester (8) by reaction with a carbodiimide and N-hydroxysuccinimide.

Still referring to FIG. 1, q is from 1 to 24. Preferably, q is from 1 to 18, and q is more preferably from 4 to 16. R$^4$ is a moiety capable of undergoing hydrolysis to provide the carboxylic acid. $R^4$ is preferably lower alkyl and is more preferably ethyl. The variable n is from 1 to 5, and the variable m is from 1 to 5.

Figure 2:
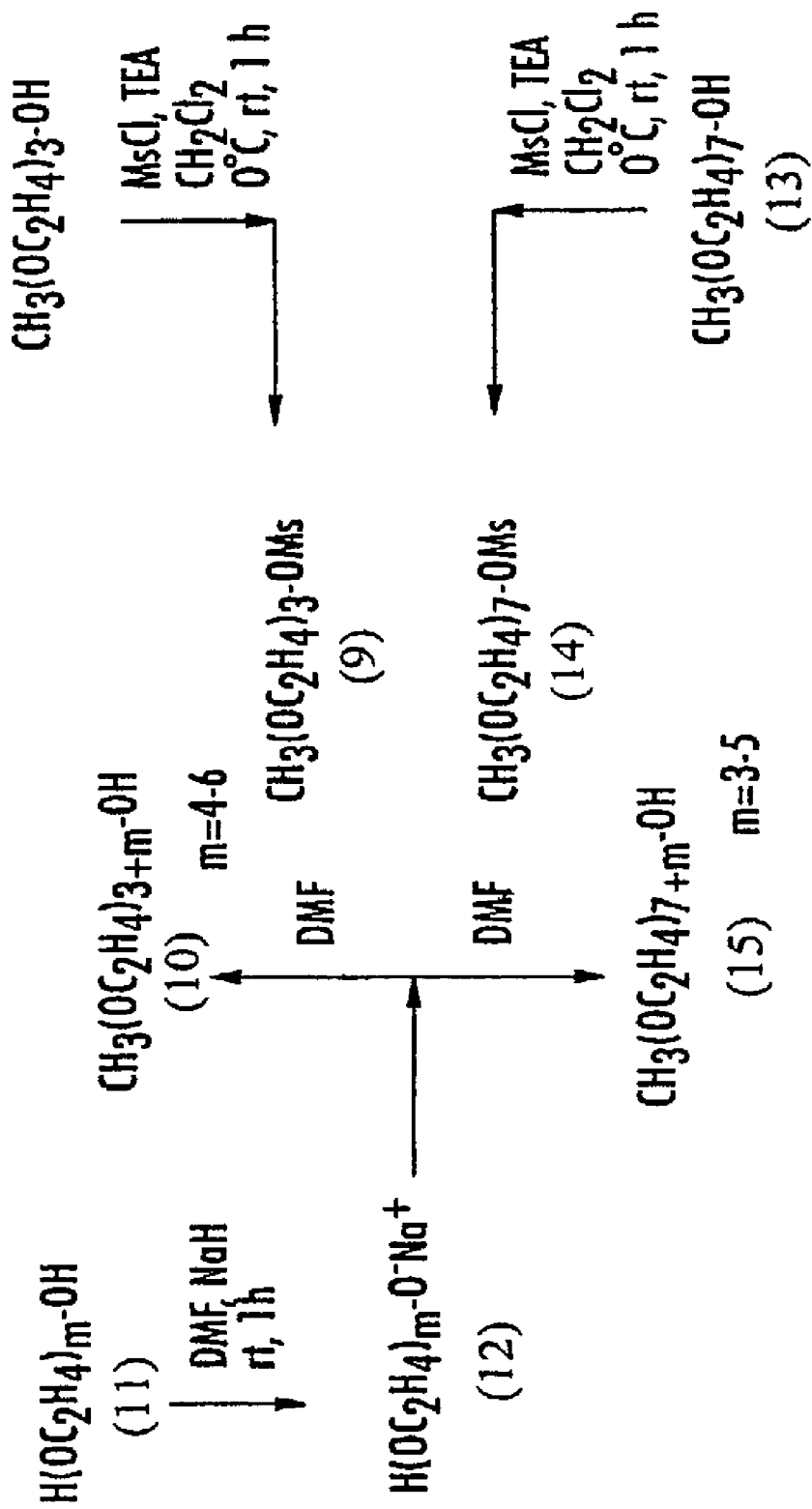
FIG. 2 illustrates a scheme for synthesizing a mixture of mPEG according to embodiments of the present invention.

Alternatively, non-polydispersed oligomers may be synthesized by synthesizing non-polydispersed polyalkylene glycol, such as polyethylene glycol, using a method such as that illustrated in FIG. 2 and described in Examples 1-10 below, and, if desired, combining the non-polydispersed polyalkylene glycol with one or more other moieties, such as the additional hydrophilic moieties, lipophilic moieties, spacer moieties, linker moieties, salt-forming moieties, and terminating moieties described above, where the additional hydrophilic moiety, lipophilic moiety, spacer moiety, linker moiety, salt-forming moiety, and/or terminating moiety is also non-polydispersed. The non-polydispersed oligomers may then be activated by various methods as will be understood by those skilled in the art, for example, reacting the non-polydispersed oligomers with N-hydroxysuccinimide.

The activated oligomers may be reacted with non-polydispersed calcitonin drugs under conditions sufficient to provide non-polydispersed calcitonin drug-oligomer conjugates. A preferred synthesis is described in Example 30 hereinbelow. As will be understood by those skilled in the art, the reaction conditions (e.g., selected molar ratios, solvent mixtures and/or pH) may be controlled such that the calcitonin drug-oligomer conjugates resulting from the reaction of the non-polydispersed activated oligomers and the non-polydispersed calcitonin drugs is non-polydispersed. For example, conjugation at the amino functionality of lysine may be suppressed by maintaining the pH of the reaction solution below the $pK_a$ of lysine. Alternatively, the calcitonin drug-oligomer conjugates may be separated and isolated utilizing, for example, HPLC to provide a non-polydispersed mixture of calcitonin drug-oligomer conjugates, for example mono-, di-, or tri-conjugates. The degree of conjugation (e.g., whether the isolated molecule is a mono-, di-, or tri-conjugate) of a particular isolated conjugate may be determined and/or verified utilizing various techniques as will be understood by those skilled in the art including, but not limited to, mass spectroscopy. The particular conjugate structure (e.g., whether the oligomer is at $Lys^{11}$, $Lys^{18}$ or the N-terminus of a salmon calcitonin mono-conjugate) may be determined and/or verified utilizing various techniques as will be understood by those skilled in the art including, but not limited to, sequence analysis, peptide mapping, selective enzymatic cleavage, and/or endopeptidase cleavage.

As will be understood by those skilled in the art, one or more of the reaction sites on the calcitonin drug may be blocked by, for example, reacting the calcitonin drug with a suitable blocking reagent such as N-tert-butoxycarbonyl (t-BOC), or N-(9-fluorenylmethoxycarbonyl) (N-FMOC). This process may be preferred, for example, when the calcitonin drug is a polypeptide and it is desired to form an unsaturated conjugate (i.e., a conjugate wherein not all nucleophilic residues are conjugated) having an oligomer at the N-terminus of the polypeptide. Following such blocking, the blocked calcitonin drugs may be reacted with the activated oligomers to provide a mixture of calcitonin drug-oligomer conjugates having oligomer(s) coupled to one or more nucleophilic residues and having blocking moieties coupled to other nucleophilic residues. After the conjugation reaction, the calcitonin drug-oligomer conjugates may be de-blocked as will be understood by those skilled in the art. If desirable, the calcitoinin drug-oligomer conjugates may then be separated as described above to provide non-polydispersed calcitonin drug-oligomer conjugates. Alternatively, the calcitonin drug-oligomer conjugates may be separated prior to de-blocking.

Calcitonin drug-oligomer conjugates according to embodiments of the present invention preferably have improved properties when compared with the properties of native calcitonin or those of conventional conjugates. For example, calcitonin drug-oligomer conjugates according to embodiments of the present invention preferably are capable of lowering serum calcium levels by at least 5 percent. Preferably, the conjugates are capable of lowering serum calcium levels by at least 10, 11, 12, 13 or 14 percent. More preferably, the conjugates are capable of lowering serum calcium levels by at least 15, 16, 17, 18 or 19 percent, and, most preferably, the conjugates are capable of lowering serum calcium levels by at least 20 percent.

As another example, calcitonin drug-oligomer conjugates according to embodiments of the present invention preferably have an increased resistance to degradation by chymotrypsin and/or trypsin when compared to the resistance to degradation by chymotrypsin and/or trypsin, respectively, of the calcitonin drug which is not coupled to the oligomer. Resistance to chymotrypsin or trypsin corresponds to the percent remaining when the molecule to be tested is digested in the applicable enzyme using the procedure outlined in Example 36 below. Preferably, the resistance to degradation by chymotrypsin of the calcitonin drug-oligomer conjugates is about 10 percent greater than the resistance to degradation by chymotrypsin of the calcitonin drugs that is not conjugated with the oligomer. More preferably, the resistance to degradation by chymotrypsin of the calcitonin drug-oligomer conjugates is about 15 percent greater than the resistance to degradation by chymotrypsin of the calcitonin drug that is not conjugated with the oligomer, and, most preferably, the resistance to degradation by chymotrypsin of the calcitonin drug-oligomer conjugates is about 20 percent greater than the resistance to degradation by chymotrypsin of the calcitonin drug that is not conjugated with the oligomer. Preferably, the resistance to degradation by trypsin of the calcitonin drug-oligomer conjugates is about 10 percent greater than the resistance to degradation by trypsin of the calcitonin drug that is not conjugated with the oligomer. More preferably, the resistance to degradation by trypsin of the calcitonin drug-oligomer conjugates is about 20 percent greater than the resistance to degradation by trypsin of the calcitonin drug that is not conjugated with the oligomer, and, most preferably, the resistance to degradation by trypsin of the calcitonin drug-oligomer conjugates is about 30 percent greater than the resistance to degradation by trypsin of the calcitonin drug that is not conjugated with the oligomer.

As still another example, calcitonin-oligomer conjugates according to embodiments of the present invention preferably have a higher bioefficacy than the bioefficacy of the calcitonin drug which is not coupled to the oligomer. The bioefficacy of a particular compound corresponds to its area-under-the-curve (AUC) value. Preferably, the bioefficacy of the conjugates are about 5 percent greater than the bioefficacy of the calcitonin drug which is not coupled to the oligomer. More preferably, the bioefficacy of the conjugates are about 10 percent greater than the bioefficacy of the calcitonin drug which is not coupled to the oligomer.

As yet another example, substantially monodispersed calcitonin drug-oligomer conjugates according to embodiments of the present invention preferably have an in vivo activity that is greater than the in vivo activity of a polydispersed mixture of calcitonin drug-oligomer conjugates having the same number average molecular weight as the substantially monodispersed mixture. As will be understood by those skilled in the art, the number average molecular weight of a mixture may be measured by various methods including, but not limited to, size exclusion chromatography such as gel permeation chromatography as described, for example, in H. R. Allcock & F. W. Lampe, CONTEMPORARY POLYMER CHEMISTRY 394-402 (2d. ed., 1991).

As another example, substantially monodispersed calcitonin drug-oligomer conjugates according to embodiments of the present invention preferably have an in vitro activity that is greater than the in vitro activity of a polydispersed mixture of calcitonin drug-oligomer conjugates having the same number average molecular weight as the substantially monodispersed mixture. As will be understood by those skilled in the art, the number average molecular weight of a mixture may be measured by various methods including, but not limited to, size exclusion chromatography.

As still another example, substantially monodispersed calcitonin drug-oligomer conjugates preferably have an increased resistance to degradation by chymotrypsin and/or trypsin when compared to the resistance to degradation by chymotrypsin and/or trypsin of a polydispersed mixture of calcitonin drug-oligomer conjugates having the same number average molecular weight as the substantially monodispersed mixture. As will be understood by those skilled in the art, the number average molecular weight of a mixture may be measured by various methods including, but not limited to, size exclusion chromatography.

As yet another example, substantially monodispersed calcitonin-oligomer conjugates preferably have an inter-subject variability that is less than the inter-subject variability of a polydispersed mixture of calcitonin drug-oligomer conjugates having the same number average molecular weight as the substantially monodispersed mixture. As will be understood by those skilled in the art, the number average molecular weight of a mixture may be measured by various methods including, but not limited to, size exclusion chromatography. The inter-subject variability may be measured by various methods, as will be understood by those skilled in the art. The inter-subject variability is preferably calculated as follows. The area under a dose response curve (AUC) (i.e., the area between the dose-response curve and a baseline value) is determined for each subject. The average AUC for all subjects is determined by summing the AUCs of each subject and dividing the sum by the number of subjects. The absolute value of the difference between the subject's AUC and the average AUC is then determined for each subject. The absolute values of the differences obtained are then summed to give a value that represents the inter-subject variability. Lower values represent lower inter-subject variabilities and higher values represent higher inter-subject variabilities.

Calcitonin drug-oligomer conjugates according to embodiments of the present invention preferably have two or more of the above-described improved properties. More preferably, calcitonin drug-oligomer conjugates according to embodiments of the present invention have three or more of the above-described improved properties. Most preferably, calcitonin drug-oligomer conjugates according to embodiments of the present invention have four or more of the above-described improved properties.

Pharmaceutical compositions comprising conjugates according to embodiments of the present invention are also provided. The calcitonin drug-oligomer conjugates described above may be formulated for administration in a pharmaceutical carrier in accordance with known techniques. See, e.g., Remington, *The Science And Practice of Pharmacy* ($9^{th}$ Ed. 1995). In the manufacture of a pharmaceutical composition according to embodiments of the present invention, the calcitonin drug-oligomer conjugate is typically admixed with, inter alia, a pharmaceutically acceptable carrier. The carrier must, of course, be acceptable in the sense of being compatible with any other ingredients in the pharmaceutical composition and should not be deleterious to the patient. The carrier may be a solid or a liquid, or both, and is preferably formulated with the calcitonin drug-oligomer conjugate as a unit-dose formulation, for example, a tablet, which may contain from about 0.01 or 0.5% to about 95% or 99% by weight of the calcitonin drug-oligomer conjugates. The pharmaceutical compositions may be prepared by any of the well known techniques of pharmacy including, but not limited to, admixing the components, optionally including one or more accessory ingredients.

The pharmaceutical compositions according to embodiments of the present invention include those suitable for oral, rectal, topical, inhalation (e.g., via an aerosol) buccal (e.g., sub-lingual), vaginal, parenteral (e.g., subcutaneous, intramuscular, intradermal, intraarticular, intrapleural, intraperitoneal, inracerebral, intraarterial, or intravenous), topical (i.e., both skin and mucosal surfaces, including airway surfaces) and transdermal administration, although the most suitable route in any given case will depend on the nature and severity of the condition being treated and on the nature of the particular calcitonin drug-oligomer conjugate which is being used.

Pharmaceutical compositions suitable for oral administration may be presented in discrete units, such as capsules, cachets, lozenges, or tables, each containing a predetermined amount of the calcitonin drug-oligomer conjugate; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the calcitonin drug-oligomer conjugate and a suitable carrier (which may contain one or more accessory ingredients as noted above). In general, the pharmaceutical composition according to embodiments of the present invention are prepared by uniformly and intimately admixing the calcitonin drug-oligomer conjugate with a liquid or finely divided solid carrier, or both, and then, if necessary, shaping the resulting mixture. For example, a tablet may be prepared by compressing or molding a powder or granules containing the calcitonin drug-oligomer conjugate, optionally with one or more accessory ingredients. Compressed tablets may be prepared by compressing, in a suitable machine, the mixture in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Pharmaceutical compositions suitable for buccal (sub-lingual) administration include lozenges comprising the calcitonin drug-oligomer conjugate in a flavoured base, usually sucrose and acacia or tragacanth; and pastilles comprising the calcitonin drug-oligomer conjugate in an inert base such as gelatin and glycerin or sucrose and acacia.

Pharmaceutical compositions according to embodiments of the present invention suitable for parenteral administration comprise sterile aqueous and non-aqueous injection solutions of the calcitonin drug-oligomer conjugate, which preparations are preferably isotonic with the blood of the intended recipient. These preparations may contain anti-oxidants, buffers, bacteriostats and solutes which render the composition isotonic with the blood of the intended recipient. Aqueous and non-aqueous sterile suspensions may include suspending agents and thickening agents. The compositions may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, an injectable, stable, sterile composition comprising a calcitonin drug-oligomer conjugate in a unit dosage form in a sealed container may be provided. The calcitonin drug-oligomer conjugate is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the calcitonin drug-oligomer conjugate. When the calcitonin drug-oligomer conjugate is substantially water-insoluble, a sufficient amount of emulsifying agent which is physiologically acceptable may be employed in sufficient quantity to emulsify the calcitonin drug-oligomer conjugate in an aqueous carrier. One such useful emulsifying agent is phosphatidyl choline.

Pharmaceutical compositions suitable for rectal administration are preferably presented as unit dose suppositories. These may be prepared by admixing the calcitonin drug-oligomer conjugate with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Pharmaceutical compositions suitable for transdermal administration may be presented as discrete patches adapted to remain in intimate contact with the epidermis of the recipient for a prolonged period of time. Compositions suitable for transdermal administration may also be delivered by iontophoresis (see, for example, *Pharmaceutical Research* 3 (6): 318 (1986)) and typically take the form of an optionally buffered aqueous solution of the calcitonin drug-oligomer conjugate. Suitable formulations comprise citrate or bis\tris buffer (pH 6) or ethanol/water and contain from 0.1 to 0.2M active ingredient.

Methods of treating a bone disorder in a subject in need of such treatment by administering an effective amount of such pharmaceutical compositions are also provided. The bone disorder is preferably characterized by excessive osteoclastic bone resorption and/or hypercalcemic serum effects. Bone disorders that may be treated and/or prevented by methods of the present invention include, but are not limited to, osteoporosis, Paget's disease, and hypercalcemia.

The effective amount of any calcitonin drug-oligomer conjugate, the use of which is in the scope of present invention, will vary somewhat from conjugate to conjugate, and patient to patient, and will depend upon factors such as the age and condition of the patient and the route of delivery. Such dosages can be determined in accordance with routine pharmacological procedures known to those skilled in the art. As a general proposition, a dosage from about 0.1 to about 50 mg/kg will have therapeutic efficacy, with all weights being calculated based upon the weight of the calcitonin drug-oligomer conjugate. Toxicity concerns at the higher level may restrict intravenous dosages to a lower level such as up to about 10 mg/kg, with all weights being calculated based upon the weight of the active base. A dosage from about 10 mg/kg to about 50 mg/kg may be employed for oral administration. Typically, a dosage from about 0.5 mg/kg to 5 mg/kg may be employed for intramuscular injection. The frequency of administration is usually one, two, or three times per day or as necessary to control the condition. Alternatively, the drug-oligomer conjugate may be administered by continuous infusion. The duration of treatment depends on the type of bone disorder being treated and may be for as long as the life of the patient.

All starting materials used in the procedures described herein are either commercially available or can be prepared by methods known in the art using commercially available starting materials.

The present invention will now be described with reference to the following examples. It should be appreciated that these examples are for the purposes of illustrating aspects of the present invention, and do not limit the scope of the invention as defined by the claims.

EXAMPLES

Examples 1 through 10

Reactions in Examples 1 through 10 were carried out under nitrogen with magnetic stirring, unless otherwise specified. "Work-up" denotes extraction with an organic solvent, washing of the organic phase with saturated NaCl solution, drying ($MgSO_4$), and evaporation (rotary evaporator). Thin layer chromatography was conducted with Merck glass plates pre-coated with silica gel 60° F.-254 and spots were visualized by iodine vapor. All mass spectra were determined by Macromolecular Resources Colorado State University, CO and are reported in the order m/z, (relative intensity). Elemental analyses and melting points were performed by Galbraith Laboratories, Inc., Knoxville, Tenn. Examples 1-10 refer to the scheme illustrated in FIG. 2.

Example 1

8-Methoxy-1-(methylsulfonyl)oxy-3,6-dioxaoctane (9)

A solution of non-polydispersed triethylene glycol monomethyl ether molecules (4.00 mL, 4.19 g, 25.5 mmol) and triethylamine (4.26 mL, 3.09 g, 30.6 mmol) in dry dichloromethane (50 mL) was chilled in an ice bath and place under a nitrogen atmosphere. A solution of methanesulfonyl chloride (2.37 mL, 3.51 g, 30.6 mmol) in dry dichloromethane (20 mL) was added dropwise from an addition funnel. Ten minutes after the completion of the chloride addition, the reaction mixture was removed from the ice bath and allowed to come to room temperature. The mixture was stirred for an additional hour, at which time TLC ($CHCl_3$ with 15% MeOH as the elutant) showed no remaining triethylene glycol monomethyl ether.

The reaction mixture was diluted with another 75 mL of dichloromethane and washed successively with saturated $NaHCO_3$, water and brine. The organics were dried over Na$_2$SO$_4$, filtered and concentrated in vacuo to give a non-polydispersed mixture of compounds 9 as a clear oil (5.31 g, 86%).

Example 2

Ethylene glycol mono methyl ether (10) (m=4,5,6)

To a stirred solution of non-polydispersed compound 11 (35.7 mmol) in dry DMF (25.7 mL), under N$_2$ was added in portion a 60% dispersion of NaH in mineral oil, and the mixture was stirred at room temperature for 1 hour. To this salt 12 was added a solution of non-polydispersed mesylate 9 (23.36) in dry DMF (4 ml) in a single portion, and the mixture was stirred at room temperature for 3.5 hours. Progress of the reaction was monitored by TLC (12% CH$_3$OH—CHCl$_3$). The reaction mixture was diluted with an equal amount of 1N HCl, and extracted with ethyl acetate (2×20 ml) and discarded. Extraction of aqueous solution and work-up gave non-polydispersed polymer 10 (82-84% yield).

Example 3

3,6,9,12,15,18,21-Heptaoxadocosanol (10) (m=4)

Oil; Rf 0.46 (methanol:chloroform=3:22); MS m/z calc'd for C$_{15}$H$_{32}$O$_8$ 340.21 (M$^+$+1), found 341.2.

Example 4

3,6,9,12,15,18,21,24-Octaoxapentacosanol (10) (m=5)

Oil; Rf 0.43 (methanol:chloroform=6:10); MS m/z calc'd for C$_{17}$H$_{36}$O$_9$ 384.24 (M$^+$+1), found 385.3.

Example 5

3,6,9,12,15,18,21,24,27-Nonaoxaoctacosanol (10) (m=6)

Oil; Rf 0.42 (methanol:chloroform=6:10); MS m/z calc'd for C$_{19}$H$_{40}$O$_{10}$ 428.26 (M$^+$+1), found 429.3.

Example 6

20-methoxy-1-(methylsulfonyl)oxy-3,6,9,12,15,18-hexaoxaeicosane (14)

Non-polydispersed compound 14 was obtained in quantitative yield from the alcohol 13 (m=4) and methanesulfonyl chloride as described for 9, as an oil; Rf 0.4 (ethyl acetate: acetonitrile=1:5); MS m/z calc'd for C$_{17}$H$_{37}$O$_{10}$ 433.21 (M$^+$+1), found 433.469.

Example 7

Ethylene glycol mono methyl ether (15) (m=3,4,5)

The non-polydispersed compounds 15 were prepared from a diol by using the procedure described above for compound 10.

Example 8

3,6,9,12,15,18,21,24,27,30-Decaoxaheneicosanol (15) (m=3)

Oil; Rf 0.41 (methanol:chloroform=6:10); MS m/z calc'd for C$_{21}$H$_{44}$O$_{11}$ 472.29 (M$^+$+1), found 472.29.

Example 9

3,6,9,12,15,18,21,24,27,30,33-Unecaoxatetratricosanol (15) (m=4)

Oil; Rf 0.41 (methanol:chloroform=6:10); MS m/z calc'd for C$_{23}$H$_{48}$O$_{12}$ 516.31 (M$^+$+1), found 516.31.

Example 10

3,6,9,12,15,18,21,24,27,30,33,36-Dodecaoxaheptatricosanol (15) (m=5)

Oil; Rf 0.41 (methanol:chloroform=6:10); MS m/z calc'd for C$_{25}$H$_{52}$O$_{13}$ 560.67 (M$^+$+1), found 560.67.

Example 11

Mesylate of triethylene glycol monomethyl ether (16)

To a solution of CH$_2$Cl$_2$ (100 mL) cooled to 0° C. in an ice bath was added non-polydispersed triethylene glycol monomethyl ether (25 g, 0.15 mol). Then triethylamine (29.5 mL, 0.22 mol) was added and the solution was stirred for 15 min at 0° C., which was followed by dropwise addition of methanesulfonyl chloride (13.8 mL, 0.18 mol, dissolved in 20 mL CH$_2$Cl$_2$). The reaction mixture was stirred for 30 min at 0° C., allowed to warm to room temperature, and then stirred for 2 h. The crude reaction mixture was filtered through Celite (washed CH$_2$Cl$_2$~200 mL), then washed with H$_2$O (300 mL), 5% NaHCO$_3$ (300 mL), H$_2$O (300 mL), sat. NaCl (300 mL), dried MgSO$_4$, and evaporated to dryness. The oil was then placed on a vacuum line for ~2 h to ensure dryness and afforded the non-polydispersed title compound as a yellow oil (29.15 g, 80% yield).

Example 12

Heptaethylene glycol monomethyl ether (17)

To a solution of non-polydispersed tetraethylene glycol (51.5 g, 0.27 mol) in THF (1L) was added potassium t-butoxide (14.8 g, 0.13 mol, small portions over ~30 min). The reaction mixture was then stirred for 1 h and then 16 (29.15 g, 0.12 mol) dissolved in THF (90 mL) was added dropwise and the reaction mixture was stirred overnight. The crude reaction mixture was filtered through Celite (washed CH$_2$Cl$_2$, ~200 mL) and evaporated to dryness. The oil was then dissolved in HCl (250 mL, 1 N) and washed with ethyl acetate (250 mL) to remove excess 16. Additional washings of ethyl acetate (125 mL) may be required to remove remaining 16. The aqueous phase was washed repetitively with CH$_2$Cl$_2$ (125 mL volumes) until most of the 17 has been removed from the aqueous phase. The first extraction will contain 16, 17, and dicoupled side product and should be back extracted with HCl (125 mL, 1N). The organic layers were combined and evaporated to dryness. The resultant oil was then dissolved in CH$_2$Cl$_2$ (100 mL) and washed repetitively with H$_2$O (50 mL volumes) until 17 was removed. The aqueous fractions were combined, total volume 500 mL, and NaCl was added until the solution became cloudy and then was washed with CH$_2$Cl$_2$ (2×500 mL). The organic layers were combined, dried MgSO$_4$, and evaporated to dryness to afford a the non-polydispersed title compound as an oil (16.9 g, 41% yield). It may be desirable to repeat one or more steps of the purification procedure to ensure high purity.

Example 13

8-Bromooctoanate (18)

To a solution of 8-bromooctanoic acid (5.0 g, 22 mmol) in ethanol (100 mL) was added $H_2SO_4$ (0.36 mL, 7.5 mmol) and the reaction was heated to reflux with stirring for 3 h. The crude reaction mixture was cooled to room temperature and washed $H_2O$ (100 mL), sat. $NaHCO_3$ (2×100 mL), $H_2O$ (100 mL), dried $MgSO_4$, and evaporated to dryness to afford a clear oil (5.5 g, 98% yield).

Example 14

Synthesis of MPEG7-C8 ester (19)

To a solution of the non-polydispersed compound 17 (3.0 g, 8.8 mmol) in ether (90 mL) was added potassium t-butoxide (1.2 g, 9.6 mmol) and the reaction mixture was stirred for 1 h. Then dropwise addition of the non-polydispersed compound 18 (2.4 g, 9.6 mmol), dissolved in ether (10 mL), was added and the reaction mixture was stirred overnight. The crude reaction mixture was filtered through Celite (washed $CH_2Cl_2$, ~200 mL) and evaporated to dryness. The resultant oil was dissolved in ethyl acetate and washed $H_2O$ (2×200 mL), dried $MgSO_4$, and evaporated to dryness. Column chromatography (Silica, ethyl acetate to ethyl acetate/methanol, 10:1) was performed and afforded the non-polydispersed title compound as a clear oil (0.843 g, 19% yield).

Example 15

MPEG7-C8 acid (20)

To the oil of the non-polydispersed compound 19 (0.70 g, 1.4 mmol) was added 1N NaOH (2.0 mL) and the reaction mixture was stirred for 4 h. The crude reaction mixture was concentrated, acidified (pH~2), saturated with NaCl, and washed $CH_2Cl_2$ (2×50 mL). The organic layers were combined, washed sat. NaCl, dried $MgSO_4$, and evaporated to dryness to afford the non-polydispersed title compound as a clear oil (0.35 g, 53% yield).

Example 16

Activation of MPEG7-C8 acid (21)

Non-polydispersed mPEG7-C8-acid 20 (0.31 g, 0.64 mmol) was dissolved in 3 ml of anhydrous methylene chloride and then solution of N-hydroxysuccinimide (0.079 g, 0.69 mmol) and EDCI.HCl (135.6 mg, 0.71 mmol) in anhydrous methylene chloride added. Reaction was stirred for several hours, then washed with 1N HCl, water, dried over $MgSO_4$, filtered and concentrated. Crude material was purified by column chromatography, concentrated to afford the non-polydispersed title compound as a clear oil and dried via vacuum.

Example 17

10-hydroxydecanoate (22)

To a solution of non-polydispersed 10-hydroxydecanoic acid (5.0 g, 26.5 mmol) in ethanol (100 mL) was added $H_2SO_4$ (0.43 mL, 8.8 mmol) and the reaction was heated to reflux with stirring for 3 h. The crude reaction mixture was cooled to room temperature and washed $H_2O$ (100 mL), sat. $NaHCO_3$ (2×100 mL), $H_2O$ (100 mL), dried $MgSO_4$, and evaporated to dryness to afford the non-polydispersed title compound as a clear oil (6.9 g, 98% yield).

Example 18

Mesylate of 10-hydroxydecanoate (23)

To a solution of $CH_2Cl_2$ (27 mL) was added non-polydispersed 10-hydroxydecanoate 22 (5.6 g, 26 mmol) and cooled to 0° C. in an ice bath. Then triethylamine (5 mL, 37 mmol) was added and the reaction mixture was stirred for 15 min at 0° C. Then methanesulfonyl chloride (2.7 mL, 24 mmol) dissolved in $CH_2Cl_2$ (3 mL) was added and the reaction mixture was stirred at 0° C. for 30 min, the ice bath was removed and the reaction was stirred for an additional 2 h at room temperature. The crude reaction mixture was filtered through Celite (washed $CH_2Cl_2$, 80 mL) and the filtrate was washed $H_2O$ (100 mL), 5% $NaHCO_3$ (2×100 mL), $H_2O$ (100 mL), sat. NaCl (100 mL), dried $MgSO_4$, and evaporated to dryness to afford the non-polydispersed title compound as a yellowish oil (7.42 g, 97% yield).

Example 19

$MPEG_7$-$C_{10}$ Ester (24)

To a solution of non-polydispersed heptaethylene glycol monomethyl ether 17 (2.5 g, 7.3 mmol) in tetrahydrofuran (100 mL) was added sodium hydride (0.194 g, 8.1 mmol) and the reaction mixture was stirred for 1 h. Then dropwise addition of mesylate of non-polydispersed 10-hydroxydecanoate 23 (2.4 g, 8.1 mmol), dissolved in tetrahydrofuran (10 mL), was added and the reaction mixture was stirred overnight. The crude reaction mixture was filtered through Celite (washed $CH_2Cl_2$, ~200 mL) and evaporated to dryness. The resultant oil was dissolved in ethyl acetate and washed $H_2O$ (2×200 mL), dried $MgSO_4$, evaporated to dryness, chromatographed (silica, ethyl acetate/methanol, 10:1), and chromatographed (silica, ethyl acetate) to afford the non-polydispersed title compound as a clear oil (0.570 g, 15% yield).

Example 20

$MPEG_7$-$C_{10}$ Acid (25)

To the oil of non-polydispersed $mPEG_7$-$C_{10}$ ester 24 (0.570 g, 1.1 mmol) was added 1N NaOH (1.6 mL) and the reaction mixture was stirred overnight. The crude reaction mixture was concentrated, acidified (pH~2), saturated with NaCl, and washed $CH_2Cl_2$ (2×50 mL). The organic layers were combined, washed sat. NaCl (2×50 mL), dried $MgSO_4$, and evaporated to dryness to afford the non-polydispersed title compound as a clear oil (0.340 g, 62% yield).

Example 21

Activation of $MPEG_7$-$C_{10}$ Acid (26)

The non-polydispersed acid 25 was activated using procedures similar to those described above in Example 16.

Example 22

Synthesis of C18(PEG6) Oligomer (27)

Non-polydispersed stearoyl chloride (0.7 g, 2.31 mmol) was added slowly to a mixture of PEG6 (5 g, 17.7 mmol) and pyridine (0.97 g, 12.4 mmol) in benzene. The reaction mixture was stirred for several hours (~5). The reaction was followed by TLC using ethylacetate/methanol as a developing solvent. Then the reaction mixture was washed with water, dried over $MgSO_4$, concentrated and dried via vacuum. Purified non-polydispersed compound 27 was analyzed by FABMS: m/e 549/M+H.

Example 23

Activation of C18(PEG6) Oligomer

Activation of non-polydispersed C18(PEG6) oligomer was accomplished in two steps:

1) Non-polydispersed stearoyl-PEG6 27 (0.8 g, 1.46 mmol ) was dissolved in toluene and added to a phosgene solution (10 ml, 20% in toluene) which was cooled with an ice bath. The reaction mixture was stirred for 1 h at 0° C. and then for 3 h at room temperature. Then phosgene and toluene were distilled off and the remaining non-polydispersed stearoyl PEG6 chloroformate 28 was dried over $P_2O_5$ overnight.

2) To a solution of non-polydispersed stearoyl PEG6 chloroformate 29 (0.78 g, 1.27 mmol) and TEA (128 mg, 1.27 mmol) in anhydrous methylene chloride, N-hydroxy succinimide (NHS) solution in methylene chloride was added. The reaction mixture was stirred for 16 hours, then washed with water, dried over $MgSO_4$, filtered, concentrated and dried via vacuum to provide the non-polydispersed activated C18 (PEG6) oligomer 30.

Example 24

Tetraethylene glycol monobenzylether (31)

To the oil of non-polydispersed tetraethylene glycol (19.4 g, 0.10 mol) was added a solution of NaOH (4.0 g in 4.0 mL) and the reaction was stirred for 15 mm. Then benzyl chloride (3.54 mL, 30.8 mmol) was added and the reaction mixture was heated to 100° C. and stirred overnight. The reaction mixture was cooled to room temperature, diluted with sat. NaCl (250 mL), and washed $CH_2Cl_2$ (2×200 mL). The organic layers were combined, washed sat. NaCl, dried $MgSO_4$, and chromatographed (silica, ethyl acetate) to afford the non-polydispersed title compound as a yellow oil (6.21 g, 71% yield).

Example 25

Mesylate of tetraethylene glycol monobenzylether (32)

To a solution of $CH_2Cl_2$ (20 mL) was added non-polydispersed tetraethylene glycol monobenzylether 31 (6.21 g, 22 mmol) and cooled to 0° C. in an ice bath. Then triethylamine (3.2 mL, 24 mmol) was added and the reaction mixture was stirred for 15 min at 0° C. Then methanesulfonyl chloride (1.7 mL, 24 mmol) dissolved in $CH_2Cl_2$ (2 mL) was added and the reaction mixture was stirred at 0° C. for 30 min, the ice bath was removed and the reaction was stirred for an additional 2 h at room temperature. The crude reaction mixture was filtered through Celite (washed $CH_2Cl_2$, 80 mL) and the filtrate was washed $H_2O$ (100 mL), 5% $NaHCO_3$ (2×100 mL), $H_2O$ (100 mL), sat. NaCl (100 mL), and dried $MgSO_4$. The resulting yellow oil was chromatographed on a pad of silica containing activated carbon (10 g) to afford the non-polydispersed title compound as a clear oil (7.10 g, 89% yield).

Example 26

Octaethylene glycol monobenzylether (33)

To a solution of tetrahydrofuran (140 mL) containing sodium hydride (0.43 g, 18 mmol) was added dropwise a solution of non-polydispersed tetraethylene glycol (3.5 g, 18 mmol) in tetrahydrofuran (10 mL) and the reaction mixture was stirred for 1 h. Then mesylate of non-polydispersed tetraethylene glycol monobenzylether 32 (6.0 g, 16.5 mmol) dissolved in tetrahydrofuran (10 mL) was added dropwise and the reaction mixture was stirred overnight. The crude reaction mixture was filtered through Celite (washed, $CH_2Cl_2$, 250 mL) and the filtrate was washed $H_2O$, dried $MgSO_4$, and evaporated to dryness. The resultant oil was chromatographed (silica, ethyl acetate/methanol, 10:1) and chromatographed (silica, chloroform/methanol, 25:1) to afford the non-polydispersed title compound as a clear oil (2.62 g, 34% yield).

Example 27

Synthesis of Stearate PEG8-Benzyl (35)

To a stirred cooled solution of non-polydispersed octaethylene glycol monobenzylether 33 (0.998 g, 2.07 mmol) and pyridine (163.9 mg, 2.07 mmol) was added non-polydispersed stearoyl chloride 34 (627.7 mg, 2.07 mmol) in benzene. The reaction mixture was stirred overnight (18 hours). The next day the reaction mixture was washed with water, dried over $MgSO_4$, concentrated and dried via vacuum. Then the crude product was chromatographed on flash silica gel column, using 10% methanol/90% chloroform. The fractions containing the product were combined, concentrated and dried via vacuum to afford the non-polydispersed title compound.

Example 28

Hydrogenolysis of Stearate-PEG8-Benzyl

To a methanol solution of non-polydispersed stearate-PEG8-Bzl 35 (0.854 g 1.138 mmol ) Pd/C(10%) (palladium, 10% wt. on activated carbon) was added. The reaction mixture was stirred overnight (18 hours) under hydrogen. Then the solution was filtered, concentrated and purified by flash column chromatography using 10% methanol/90% chloroform, fractions with $R_f$=0.6 collected, concentrated and dried to provide the non-polydispersed acid 36.

Example 29

Activation of C18(PEG8) Oligomer

Two step activation of non-polydispersed stearate-PEG8 oligomer was performed as described for stearate-PEG6 in Example 23 above to provide the non-polydispersed activated C18(PEG8) oligomer 37.

Example 30

150 mg of salmon calcitonin (MW 3432, 0.043 mmol) was dissolved in 30 ml of anhydrous DMF. Then TEA (35 µL) and the activated oligomer of Example 16 (42 mg, 0.067 mmol) in anhydrous THF (2 mL) was added. The reaction was stirred for 1 hour, then quenched with 2 mL of 0.1% TFA in water.

The reaction was followed by HPLC. Then the reaction mixture was concentrated and purified by prep. HPLC (RC Vydac C18 Protein and peptide, 1×25 column, water/acetonitrile with 0.1% TFA, detection at 280 nm). Two peaks, corresponding to mono- and di-conjugate were isolated. Samples were analyzed by MALDI-MS. MS for PEG7-octyl-sCT, mono-conjugate: 3897. MS for PEG7-octyl-sCT, di-conjugate: 4361.

Example 31

The procedure of Example 30 was used to conjugate salmon calcitonin with the activated oligomer of Example 21. MS for PEG7-decyl-sCT, mono-conjugate: 3926. MS for PEG7-decyl-sCT, di-conjugate: 4420.

Example 32

The procedure of Example 30 was used to conjugate salmon calcitonin with the activated oligomer of Example 23. MS for stearate-PEG6-sCT, mono-conjugate: 4006. MS for stearate-PEG6-sCT, di-conjugate: 4582.

Example 33

The procedure of Example 30 was used to conjugate salmon calcitonin with the activated oligomer of Example 29. MS for stearate-PEG8-sCT, mono-conjugate: 4095.

Example 34

Determination of the Dispersity Coefficient for a Mixture of Salmon Calcitonin-Oligomer Conjugates The dispersity coefficient of a mixture of salmon calcitonin-oligomer conjugates is determined as follows. A mixture of salmon calcitonin-oligomer conjugates is provided, for example as described above in Example 30. A first sample of the mixture is purified via HPLC to separate and isolate the various salmon calcitonin-oligomer conjugates in the sample. Assuming that each isolated fraction contains a purely mono-dispersed mixture of conjugates, "n" is equal to the number of fractions collected. The mixture may include one or more of the following conjugates, which are described by stating the conjugation position followed by the degree of conjugation: $Lys^{11}$ monoconjugate; $Lys^{18}$ monoconjugate; N-terminus monoconjugate; $Lys^{11,18}$ diconjugate; $Lys^{11}$, N-terminus diconjugate; $Lys^{18}$, N-terminus diconjugate; and/or $Lys^{11,18}$, N-terminus triconjugate. Each isolated fraction of the mixture is analyzed via mass spectroscopy to determine the mass of the fraction, which allows each isolated fraction to be categorized as a mono-, di-, or tri-conjugate and provides a value for the variable "$M_i$" for each conjugate in the sample.

A second sample of the mixture is analyzed via HPLC to provide an HPLC trace. Assuming that the molar absorptivity does not change as a result of the conjugation, the weight percent of a particular conjugate in the mixture is provided by the area under the peak of the HPLC trace corresponding to the particular conjugate as a percentage of the total area under all peaks of the HPLC trace. The sample is collected and lyophilized to dryness to determine the anhydrous gram weight of the sample. The gram weight of the sample is multiplied by the weight percent of each component in the sample to determine the gram weight of each conjugate in the sample. The variable "$N_i$" is determined for a particular conjugate (the $i^{th}$ conjugate) by dividing the gram weight of the particular conjugate in the sample by the mass of the particular conjugate and multiplying the quotient by Avagadro's number ($6.02205 \times 10^{23}$ mole$^{-1}$), $M_i$, determined above, to give the number of molecules of the particular conjugate, $N_i$, in the sample. The dispersity coefficient is then calculated using n, $M_i$ as determined for each conjugate, and $N_i$ as determined for each conjugate.

Example 35

Cytosensor® Studies

Figure 3:
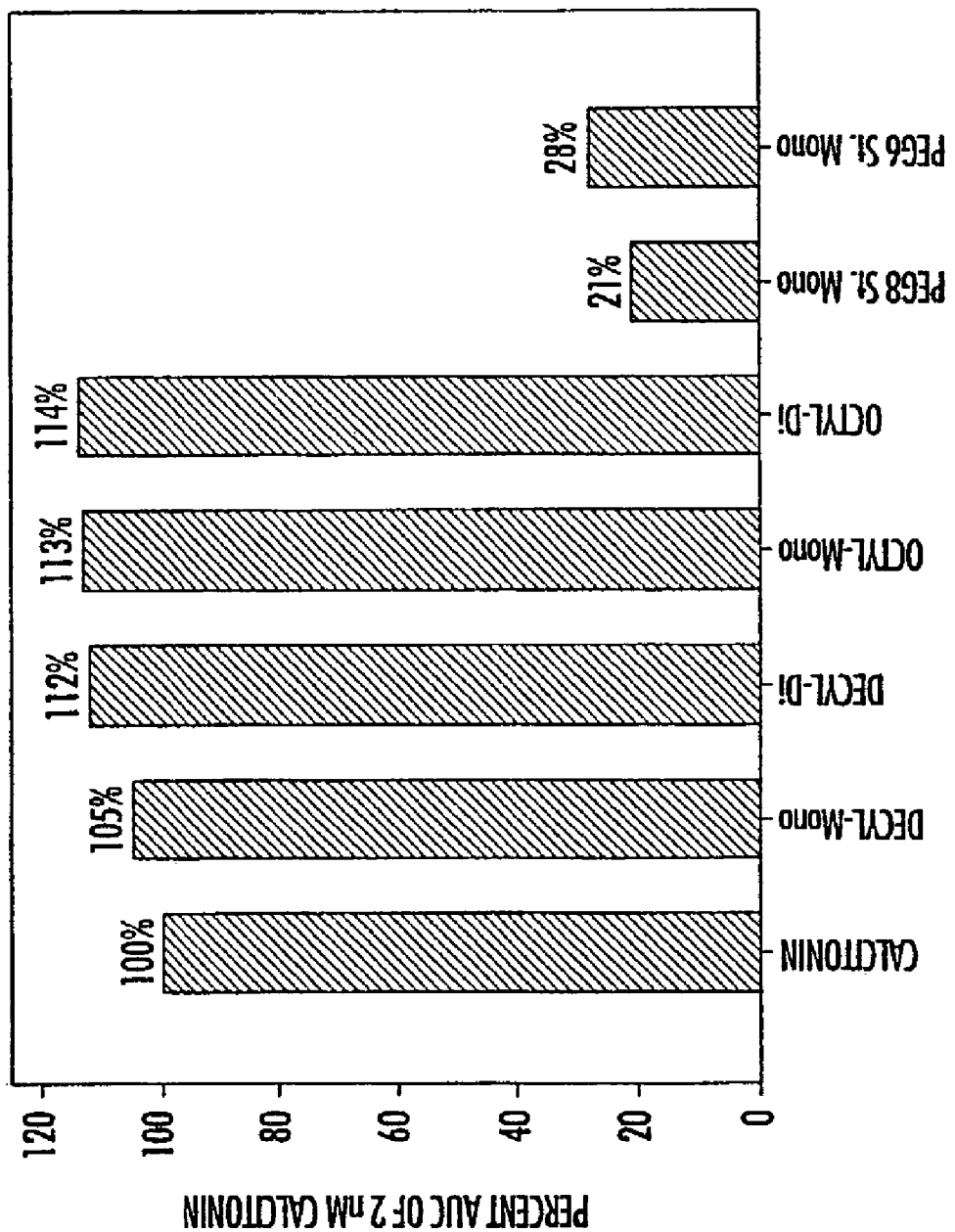
FIG. 3 illustrates a comparison of the average AUCs for various of calcitonin drug-oligomer conjugates according to embodiments of the present invention with non-conjugated calcitonin, which is provided for comparison purposes only and does not form part of the invention.
Figure 4:
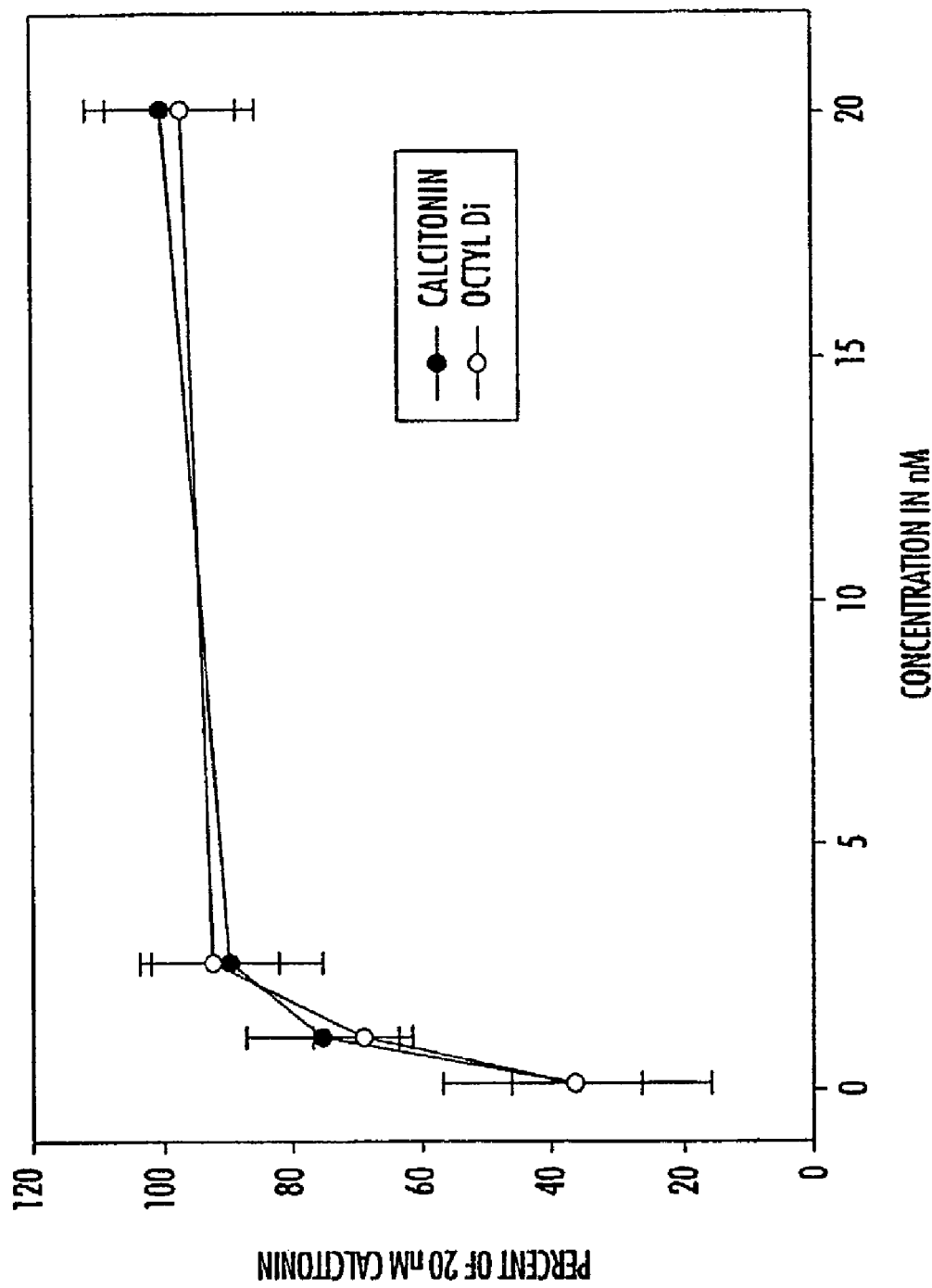
FIG. 4 illustrates a dose-response curve for mPEG7-octyl-calcitonin diconjugates according to embodiments of the present invention compared with a dose-response curve for calcitonin, which is provided for comparison purposes and is not a part of the present invention.
Figure 5:
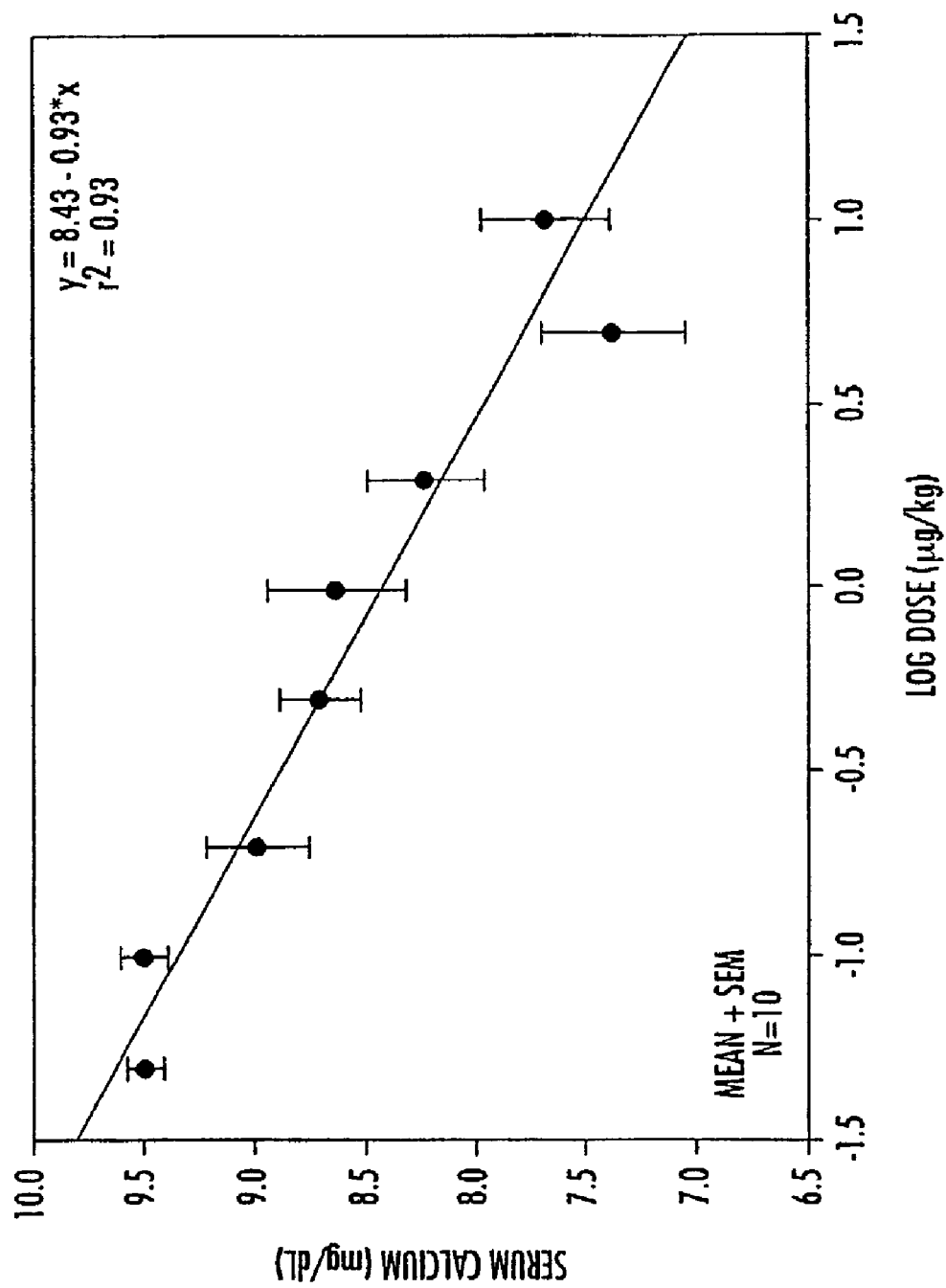
FIG. 5 illustrates a dose-response curve after oral administration of mPEG7-octyl-calcitonin diconjugates according to embodiments of the present invention.
Figure 6:
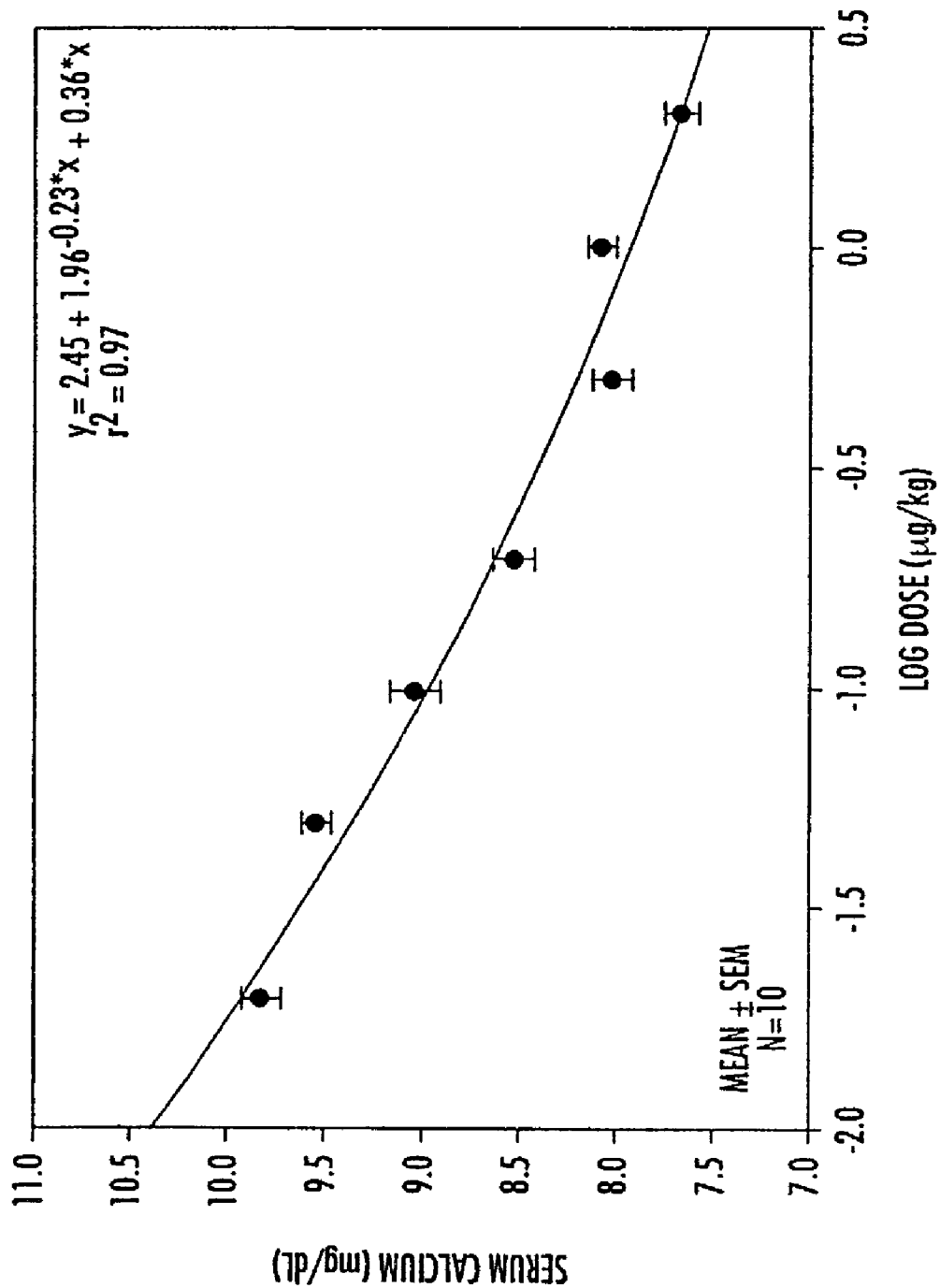
FIG. 6 illustrates a dose-response curve after subcutaneous administration of mPEG7-octyl-calcitonin diconjugates according to embodiments of the present invention.
Figure 7:
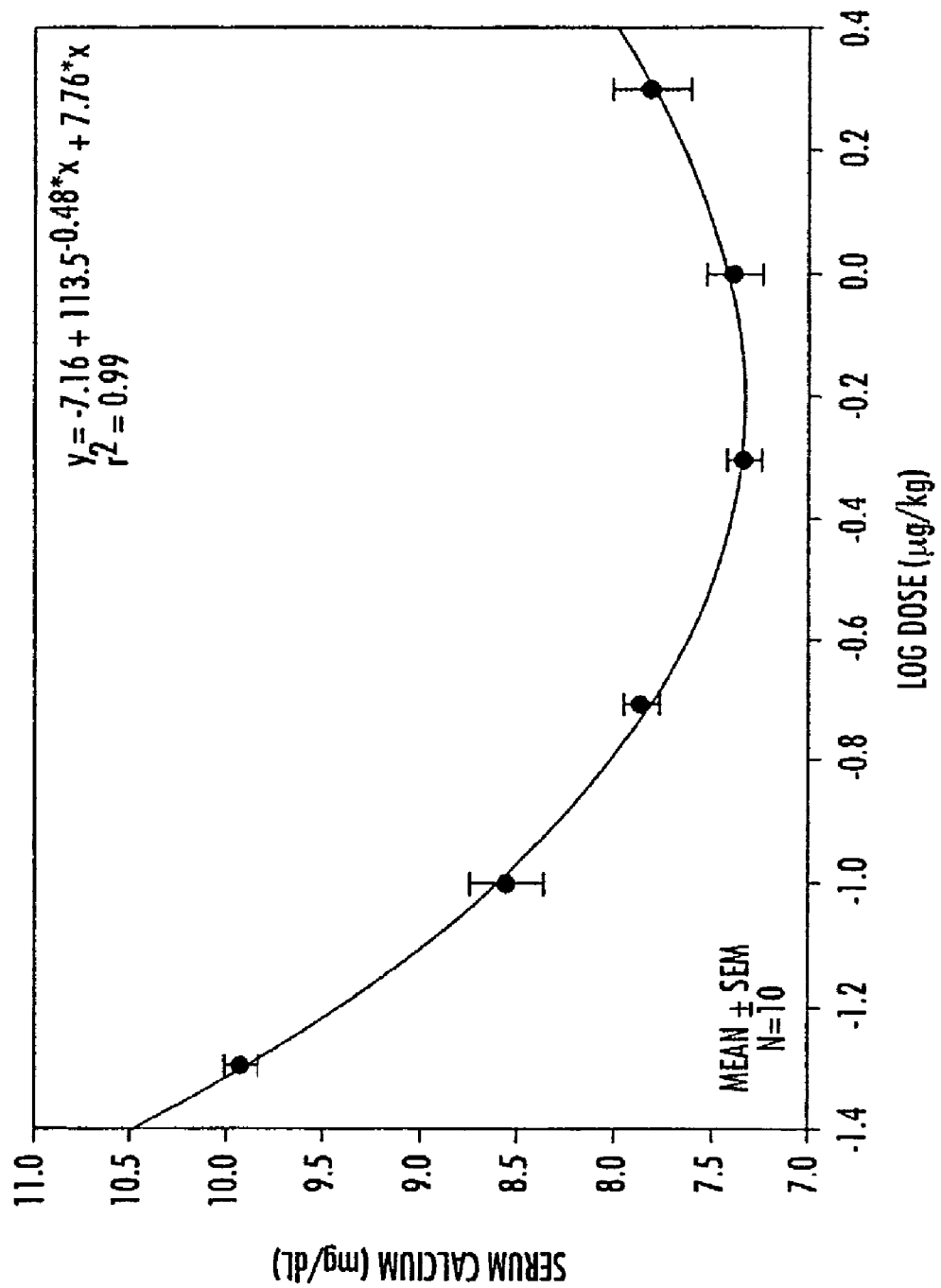
FIG. 7 illustrates a dose-response curve after subcutaneous administration of salmon calcitonin, which is provided for comparison purposes and is not part of the present invention.

T-47D cells (mammary ductal carcinoma cell line, obtained from American Type Culture Collection were suspended at a density of $1 \times 10^7$ cells/mL in running buffer (low-buffered, serum-free, bicarbonate-free RPMI 1640 medium from Molecular Devices of Sunnyvale, Calif. Approximately 100,000 cells were then immobilized in an agarose cell entrapment medium in a 10 μL droplet and sandwiched between two 3-μm polycarbonate membranes in a cytosensor capsule cup. Cytosensor capsule cups placed in sensor chambers on the Cytosensor® Microphysiometer were then held in very close proximity to pH-sensitive detectors. Running buffer was then pumped across the cells at a rate of 100 μL/min except during 30-second intervals when the flow was stopped, and acidification of the running buffer in the sensor chamber was measured. Acidification rates were determined every 2 minutes. The temperature of the sensor chambers was 37° C. Cells were allowed to equilibrate in the sensor chambers for 2-3 hours prior to the start of the experiment during which time basal acidification rates were monitored. Cells were then exposed to test compounds (Salmon Calcitonin or Octyl-Di-Calcitonin) diluted in running buffer at various nM concentration. Exposure of cells to test compounds occurred for the first 40 seconds of each 2 minute pump cycle in a repeating pattern for a total of 20 minutes. This allowed sufficient exposure of the cells to the test compounds to elicit a receptor-mediated response in cellular metabolism followed by approximately 50 seconds of flow of the running buffer containing no compounds. This procedure rinsed away test solutions (which had a slightly lower pH than running buffer alone) from the sensor chamber before measuring the acidification rate. Thus, the acidification rates were solely a measure of cellular activity. A similar procedure was used to obtain data for PEG7-octyl-sCT, monoconjugate (Octyl-Mono); PEG7-decyl-sCT, monoconjugate (Decyl-Mono); PEG7-decyl-sCT, diconjugate (Decyl-Di); stearate-PEG6-sCT, monoconjugate (PEG6 St. Mono); and stearate-PEG8-sCT, monoconjugate (PEG8 St. Mono). Data was analyzed for relative activity of compounds by calculating the Area Under the Curve (AUC) for each cytosensor chamber acidification rate graph and plotted as a bar chart illustrated in FIG. 3 showing average AUC measurements taken from multiple experiments performed under the same experimental conditions.

Example 36

Enzymatic Stability

Compounds, supplied as lyophilized powders, are resuspended in 10 mM phosphate buffer pH 7.4 and then submitted for concentration determination by HPLC. The phosphate buffer is used to create a solution with a pH that is optimum for activity of each particular gut enzyme. Aliquots of the compound thus prepared are transferred to 1.7 mL microcentrifuge tubes and shaken in a 37° C. water bath for 15 minutes to allow compounds to equilibrate to temperature. After 15 minutes, 2 μL of the appropriate concentrated gut enzyme is added to each tube to achieve the final concentration desired. Chymotrypsin and trypsin are resuspended in 1 mM HCl. Also, as a control, compounds are treated with 2 μL of 1 mM HCl. Immediately following additions, 100 μL of sample is removed from the control tube and quenched with either 25 μL of chymotrypsin/trypsin quenching solution (1:11% TFA:Isopropanol). This sample will serve as T=0 min. A sampling procedure is repeated at various time intervals depending on the gut enzyme used. Chymotrypsin has 15, 30 and 60 minute samples. Trypsin has 30, 60, 120 and 180 minute samples. Once all points have been acquired, a final sample is removed from the control tube to make sure that observed degradation is not temperature or buffer related. The chymotrypsin and trypsin samples may be collected directly into HPLC vials. RP-HPLC (acetonitrile gradient) is used to determine AUC for each sample and % degradation is calculated based from the T=0 min control. The results are provided below in Tables 1 to 4.

TABLE 1

% Remaining Following 0.5 U/mL Chymotrypsin Digest of PEG7-Octyl-Salmon Calcitonin, Diconjugate

| Time | Non-Formulated | | | | Buffered Formulation | | |
| --- | --- | --- | --- | --- | --- | --- | --- |
| 15 | 63 | 71 | 68 | 69 | 88 | 86 | 88 |
| 30 | 34 | 48 | 50 | 46 | 73 | 88 | 86 |
| 60 | 6 | 15 | 20 | 15 | 61 | 69 | 84 |
| | Control | | | | Control | | |
| 60 | 104 | 88 | 97 | 103 | 116 | 104 | 101 |

TABLE 2

% Remaining Following 0.5 U/mL Chymotrypsin Digest of Salmon Calcitonin (for comparison purposes; not part of the invention)

| Time | Non-Formulated | | | | | Buffered Formulation | | |
| --- | --- | --- | --- | --- | --- | --- | --- | --- |
| 10 | 73 | | | | | | | |
| 15 | — | 55 | 62 | 35 | 66 | 59 | 91 | 92 |
| 30 | 30 | 26 | 40 | 13 | 42 | 54 | 86 | 87 |
| 60 | 1.6 | 5 | 12 | 1 | 12 | 55 | 82 | 85 |
| | Control | | | | | Control | | |
| 60 | — | 100 | 93 | 45 | 100 | 102 | 98 | 103 |

TABLE 3

% Remaining following 1 U/mL Trypsin Digest of PEG7-Octyl-Salmon Calcitonin, Diconjugate

| Time | Non-Formulated | | | |
| --- | --- | --- | --- | --- |
| 30 | 87 | 89 | 83 | 90 |
| 60 | 78 | 86 | 76 | 85 |
| 120 | 72 | 82 | 68 | 78 |
| 180 | — | 81 | 61 | 73 |
| | Control | | | |
| 60 | | 103 | 100 | |
| 120 | 106 | 105 | 99 | |
| 180 | | 104 | 99 | |

TABLE 4

% Remaining following 1 U/mL Trypsin Digest of Salmon Calcitonin (for comparison purposes; not part of the invention)

| Time | Non-Formulated | | | |
| --- | --- | --- | --- | --- |
| 30 | 80 | 50 | 82 | 87 |
| 60 | 66 | 28 | 69 | 76 |
| 120 | 44 | 7 | 46 | 59 |
| 180 | — | 2 | 31 | 46 |
| | Control | | | |
| 60 | | 41 | 101 | |
| 120 | 69 | 16 | 102 | |
| 180 | | 7 | 101 | |

Example 37

Activity and Inter-Subject Variability

Male CF-1 mice (Charles River, Raleigh, N.C.) weighing 20-25 g were housed in the Nobex vivarium in a light—(L:D cycle of 12:12, lights on at 0600 h), temperature—(21-23° C.), and humidity—(40-60% relative humidity) controlled room. Animals were permitted free access to laboratory chow (PMI Nutrition) and tap water. Mice were allowed to acclimate to housing conditions for 48-72 hours prior to the day of experiment.

Prior to dosing, mice were fasted overnight and water was provided ad libitum. Mice were randomly distributed into groups of five animals per time point and were administered a single oral dose of a PEG7-octyl-sCT, diconjugate (Octyl Di) according to the present invention or salmon calcitonin (sCT or Calcitonin) for comparison purposes. Oral doses were administered using a gavaging needle (Popper #18, 5 cm from hub to bevel) at 10 mL/kg in the following 0.2 μg/mL phosphate-buffered PEG7-octyl-sCT, diconjugate, formulation:

| Ingredient | Amount |
| --- | --- |
| PEG7-octyl-sCT, diconjugate | 20 μg |
| Sodium-cholate | 2.5 g |
| Sodium-deoxy-cholate | 2.5 g |
| Sodium phosphate buffer, 100 mM, pH 7.4 | q.s. to 100 g |

The buffered formulation was prepared by adding 80 mL of phosphate buffer in a clean tared glass beaker. The sodium cholate was slowly added to the phosphate buffer with stirring until dissolved. The deoxy cholate was then added and stirring was continued until dissolved. The PEG7-octyl-sCT, diconjugate, solution equivalent to 20 μg was added. Finally, the remaining phosphate buffer was added to achieve a final weight of 100 g. Vehicle-control mice were used in all experiments. Dose-response curves were constructed using a single time point 60 minutes after drug administration. These curves are illustrated in FIGS. 4-7.

At appropriate time points, mice were ether-anesthetized, the vena cavae exteriorized, and blood samples were obtained via a syringe fitted with a 25-gauge needle. Blood aliquots were allowed to clot at 22° C. for 1 hour, and the sera removed and pipetted into a clean receptacle. Total serum calcium was determined for each animal using a calibrated Vitros DT60 II analyzer.

Serum calcium data were plotted and pharmacokinetic parameters determined via curve-fitting techniques using SigmaPlot software (Version 4. 1). Means and standard deviations (or standard errors) were calculated and plotted to determine effect differences among dosing groups. Average serum calcium data for various conjugates are provided in Table 5 below.

TABLE 5

| Conjugate | Dispersity | % Baseline Calcium Drop at 2.0µug/kg dose |
|---|---|---|
| PEG7-Octyl-sCT, diconjugate | Monodispersed mixture | 21.0 |
| Stearate-PEG6-sCT, diconjugate | Monodispersed mixture | 16.0 |
| PEG7-Decyl-sCT, monoconjugate | Monodispersed mixture | 11.5 |
| Stearate-PEG8-sCT, diconjugate | Monodispersed mixture | 11.0 |
| PEG7-Decyl-sCT, diconjugate | Monodispersed mixture | 8.3 |

Despite an in vitro activity as determined in Example 35 above that may not be comparable with the in vitro activity of PEG7-octyl-sCT and PEG7-decyl-sCT mono- and di-conjugates, the stearate-PEG6-sCT, diconjugate, and stearate-PEG8-sCT, diconjugate, appear to have in vivo activity (as evidenced by the drops in % baseline calcium from Table 5 above) that are comparable with the in vivo activity observed for the PEG7-octyl-sCT and PEG7-decyl-sCT, mono- and di-conjugates. While not wanting to be bound by a particular theory, the improved in vivo activity of the stearate containing conjugates may indicate that these conjugates are undergoing hydrolysis in vivo to provide an active salmon calcitonin or active salmon calcitonin-PEG conjugate.

Example 38

Preparation of mPEG$_7$-C8-Salmon Calcitonin, diconjugate ("OCD") (5.2 g scale)

1. Reagents
   A. Recombinant Salmon Calcitonin
   B. N-hydroxy Succinimide activated polymer (Magellan Laboratories)
   C. Dimethylforamide(Aldrich: "Sure Seal", Catalog # 27,685-5)
   D. Triethylamine (Aldrich: 99.5%, Catalog # 47128-3)
   E. Deionized water system filtered through 0.2 micron filter
   F. Acetic acid, glacial (99.9+%, J T Baker, Catalog # 9508-05)
   G. Acetonitrile (HPLC grade, J T Baker)
   H. Trifluoroacetic Acid (99.8%, ACS reagent grade, J T Baker, Catalog # W729-07)
   I. Isopropanol (99.9+%, HPLC grade, Burdick and Jackson, Catalog # 323-4)
2. Equipment
   A. Balances
      Top loading, range 0.01-1300 g
   B. Filters
      Corning Filter units 0.45 micron, cellulose acetate membrane 1000 mL
   C. Spatulas, stainless steel (rinsed with 70% w/w ethanol and dried)
   D. Overhead stirrer with variable speed, and stirring rod with Teflon blades to fit three-necked flask (1L) with 24/40 joint
   E. 1. Three necked round bottom flasks (1L) with 24/40 joints (dried overnight >120° C.)
      2. Graduated flask (500 mL) (dried overnight >120° C.)
   F. 1. Glass funnel (50 mL) with 24/40 joint (dried overnight >120° C.)
      2. Stainless steel powder funnel (50 mL)
   G. Thermometer (range −20-50° C.) with 24/40 ground glass adapter
   H. Membrane: MWCO1000, PLAC-V, 0.1 m$^2$, Pellicon 2 mini
   I Diafiltration Apparatus (Millipore, 4-L)
   J. Lyophilizer (e.g., Model: Genesis 12; Manufacturer: VirTis) with shelf drying set up, seal filter stainless steel or Teflon lyophilizer tray
   K. Stainless steel scoop
   L. Aluminum foil (heavy duty)
   M. Analytical HPLC with gradient system (see HPLC method)
   N. Medium preparative HPLC system (flow rate: up to 30 ml/min)
   O. Vydac Semi preparative C-18 column (25 cm (1)×5 cm (d), 300A particle size, 15-20 micron pore size)
   P. Pall Gellman VacuCap® 90 Filter (0.2 micron filter membrane, Catalog # 4622)
3. Procedure
   Preparation of Calcitonin Solution
   1. Weigh 6.0 g (5.2 g net weight, 1.52 mmoles) salmon calcitonin, (the weight was adjusted for moisture content in this case 86.87%), of calcitonin onto the three necked round bottom flask (1000 mL) and set the flask onto this stirrer. Insert the thermometer onto the flask. Add DMF (420 mL) slowly to the flask while maintaining constant stirring. Allow 10 to 15 minutes of moderate stirring until a clear solution emerges while maintaining the solution at room temperature 25±4° C. Add triethylamine (1.20 mL, 8.61 mmol) and stir for another 5 minutes.
   Preparation of Activated Octyl Polymer Solution
   2. Weigh out 1.96 g (gross weight) activated octyl polymer (similar to activated mPEG7-C8 polymer described in Example 16 above) (note: the net weight of the octyl polymer is 1.77 g (3.07 mmol) based on an octyl polymer with activation 90% w/w). Dissolve the polymer in CH$_3$CN (90 mL). The mole ratio of calcitonin protein to activated polymer should be 1:2 (mole: mole).
   Reaction of Calcitonin with Activated Octyl Polymer
   3. Add the solution of activated octyl polymer rapidly to the stirred solution of calcitonin from line 1. Rinse the vial quickly with another 10 mL of CH$_3$CN and transfer the content to the reaction flask. Continue stirring for at 25±4° C. until the OCD yield is >77%. A reaction time of 2 hours would be required.
   4. Monitor the reaction by reverse phase HPLC (see HPLC "INSCOL" method) at 280 nm wavelength. Remove a 50 µl sample of reaction mixture after 30 min, dilute with 150 µl 50:50 H$_2$O/MeOH w/0.1% TFA and inject 30 µl into HPLC (use HPLC "INSCOL" method). Repeat this procedure by removing additional samples at 1 hrs and 2 hrs time points. Stop the reaction once the % of OCD has reached >77% by proceeding to line #5. If, after 3 hours, the % OCD has not reached >77%, add additional oligomer as needed.

5. Quench the reaction with 3.12 mL 50% Acetic acid/$CH_3CN$ v/v. (This contains 27.38 mmols of acetic acid). Make sure to maintain a temperature below 27° C. during the quench. Typical yields for this reaction are as follows: OCD=81%, $M_a$=<1%, $M_b$=12%, T=5%.

Dilution

6. Dilute the crude mixture from Line #5 with 4200 mL of filtered, deionized water to bring the total organic content down to less than 10% v/v. Note: the reaction contains 521 mL of total organic solvents (420 mL DMF, 1.20 mL $Et_3N$, and 100 mL $CH_3CN$). Therefore, by addition of 4200 mL of deionized water, the total organic content is diluted to 10% v/v. Adjust the pH of the solution to 4.0 using 50% acetic acid/$H_2O$ mixture.

Purification of OCD from the Crude

7. Prepare solvents: Solvent A—TEAP A
Solvent B—TEAP B
Prepare 2L of 10×TEAP Buffer stock solution by mixing;
1600 mL of $H_2O$
200 mL of concentrated $H_3PO_4$ (85.6%)
200 mL of $Et_3N$*

*the addition of $Et_3N$ usually generates heat in the mixing of the solution

Preparation of Solvent A:
From the 10×TEAP Buffer stock solution, prepare 10 L of TEAP A by mixing: 9 L of $H_2O$
1 L of 10×TEAP Buffer stock solution Preparation of Solvent B:
From the 10×TEAP Buffer stock solution, prepare 10 L of TEAP B by mixing: 8 L Acetonitrile
1.8 L of $H_2O$+200 mL of 10×TEAP Buffer stock solution 8. Purification is carried out using a C-18 preparative column (Vydac Column # 020; 5 cm×25 cm, 300A particle size, 15-20 micron pore size)using either purification method A or B (described below). Set up the C-18 preparative column on to the prep HPLC system and wash column with 70% IPA at least 5 times of column volume and rinse the column with solvent B (TEAP B) at least 5 times of column volumes, and after with solvent A (TEAP A) for at least 5 column volumes.

9. Equilibrate the column in initial conditions (see OCD Purification Method A below) over >5 column volumes at 280 nm. Inject a small sample (100 mg protein in 100 mL) into the preparative column and run at 15 ml/min, 280 nm using the following gradient to ensure the performance of the column. The chromatographic separation of this trial injection should be similar to that of the representative chromatograph attached (see page 15).

OCD Purification Method A:
Column: Vydac Column # 020; 5 cm×25 cm, 300A particle size, 15-20 micron pore size.
Column Void Volume: 400 mL
Solvent A: TEAP A
Solvent B: TEAP B

| Time (min) | Solvent A | Solvent B | Flow rate (mL/min) |
|---|---|---|---|
| Initial (0) | 60 | 40 | 15 |
| 70 | 46 | 54 | 15 |
| 110 | 38 | 62 | 15 |
| 120 | 35 | 65 | 15 |
| 130 | 20 | 80 | 15 |

A representative preparative HPLC Chromatogram and fraction analysis of this gradient have been provided.

10. Equilibrate the column at 60% Solvent A/40% Solvent B for >5 column volumes at 280 nm, and load or inject the solution from Line #6 (2.2L containing 2.2 g of protein) and elute with the gradient system above. When the first peak begins to elute, collect 30-40 mL fractions. Store the fractions immediately upon collection at 5±3° C.

11. Analyze every fraction by analytical HPLC using "20OCD2" method. Also analyze a crude mixture sample, a salmon calcitonin sample and an OCD reference sample via the same method to allow for peak identification.

12. Pool all fractions containing OCD (purity>97%). Store pooled fractions at 5±3° C. Pool all side fractions containing OCD purity<97%>77% and set aside for a reload (Line # 14)

13. Repeat Lines #10-12 loading 1.0 g to 2.5 g crude protein (1 L-2.2 L) per injection. Maximum protein load size can be determined based on resolution obtained after the analysis of the first 2.2 g run.

14. a. Combine fractions containing OCD (purity<97%).
b. Reload side fractions <97%>77% back onto the column after diluting the ACN to 20% with deionized $H_2O$. Repeat Lines #10-#12.

Desalting of the Purified>97% OCD Fractions

15. Prepare solvents as follows:
Solvent E: Prepare a solution of 0.4% $NH_4OAc$ (w/v; 16 g of ammonium acetate in 4L of $H_2O$) and filter through a Pall Gellman VacuCap® 90 Filter (0.2 micron filter membrane).
Solvent F: $CH_3CN$
Solvent G: $H_2O$
Solvent H: Prepare a solution of 0.05% acetic acid (v/v) and filter through a Pall Gellman VacuCap® 90 Filter (0.2 micron filter membrane).

16. Salt Exchange is carried out using a C-18 preparative column (Vydac Column # 020; 5 cm×25 cm, 300A particle size, 15-20 micron pore size). Set up the C-18 preparative column on to the prep HPLC system and condition the column with 70% IPA at least 5 times of column volume and rinse the column with solvent E (0.4% $NH_4OAc$) at least 5 times of column volumes.

17. Combine pools containing OCD>97% purity from all purification and reloads. Dilute the combined pools with a sufficient amount of 0.4% $NH_4OAc$ to bring down the ACN content to 15% v/v.

Desalting:
Column: Vydac Column # 020; 5 cm×25 cm, 300A particle size, 15-20 micron pore size
Column Void Volume: 400 mL
Solvent E: 0.4% $NH_4OAc$ (filtered)
Solvent F: $CH_3CN$ Solvent G: $H_2O$
Solvent H: 0.05% Acetic acid (filtered)

| Time (min) | Solvent E | Solvent F | Solvent G | Solvent H | Flow rate (mL/min) |
|---|---|---|---|---|---|
| Initial(0) | 0 | 10 | 0 | 90 | 15 |
| 20 | 0 | 10 | 0 | 90 | 15 |
| 50 | 0 | 70 | 0 | 30 | 15 |
| 80 | 0 | 80 | 0 | 20 | 15 |

18. Equilibrate the column at 100% Solvent E (0.4% $NH_4OAc$)>5 column volumes at 280 nm.
19. Load the solution from Line #17 (2.2L containing 2.2 g of protein) and wash as follows:
   a. Wash with 100% Solvent G ($H_2O$) at 60 mL/min for 30 minutes (4 column volumes)
   b. Wash with 100% Solvent E (0.4% $NH_4OAc$) at 60 mL/min for 30 minutes (4 column volumes).
20. Next, begin the gradient for desalting (above). When the first peak begins to elute, collect 100-200 mL fractions. Samples will be very concentrated. Store the fractions immediately upon collection at 5±3° C. Adjust the pH of the fractions to 4.
21. Analyze product fractions by analytical HPLC using "20OCD2" method. A crude mixture sample, a salmon calcitonin sample and an OCD reference sample should be used as the reference markers during the analysis.
22. Pool desalted product fractions (OCD>97% purity). Store combined fractions at 5±3° C. until processing by diafiltration.

Processing

23. Prepare diafiltration apparatus according to the procedure given in the Millipore Manual: "Maintenance Procedures for Pellicon and Pellicon 2 Cassette Filters" (also see attached procedure from Nobex). A brief summary of the procedure follows:
   a. Use the following membrane for diafiltration: Millipore Pellicon II "mini" filter; regenerated cellulose; Catalog # P2PLACVOL1; V-Screen; 0.1 $m^2$; 1K cutoff.
   b. Wash the membrane by flushing the retentate side with 1.2 L of water (12L per $m^2$ of membrane)
   c. Wash the filters by filtering 7 L of water out of the permeate line (70 L per $m^2$ of membrane). The takes approximately 14 hours.
   d. Sanitize the filters by circulating 0.1N NaOH (300 mL) through the apparatus for 15 minutes. Open the permeate valve and flush 0.1N NaOH through the filters for 15 minutes.
   e. Flush water through the permeate line until the pH of the permeate is 5.5-6.
24. Dilute the salt exchanged, pooled fractions (purity>97% OCD) with deionized $H_2O$ such that the $CH_3CN$ content is brought below 15% v/v. If the concentration of the pooled, diluted fractions is above 3.5 mg/mL then dilute further to 3.5 mg/mL and transfer to a diafiltration apparatus for buffer exchange. If, however, the concentration of the pooled, diluted fractions is less than 3.5 mg/mL, then transfer to a diafiltration apparatus and concentrate the solution to a volume (X) such that it reaches 3.5 mg/mL at which point buffer exchange can begin.
25. This process is to be done below 15° C. Buffer exchange is carried out by siphoning DI $H_2O$ pH=4 (acetic acid) until 6 exchanges (6×) have been done.
   The DI $H_2O$ pH=4 (acetic acid) is prepared as follows:
   Prepare a solution of deionized water pH adjusted to 4 (using acetic acid) and filter through a Pall Gellman VacuCap® 90 Filter (0.2 micron filter membrane).
26. Collect the filtrates and analyze by HPLC for protein loss using the "20OCD2" gradient system. If they contain OCD, they are saved and re-processed separately as described in Line # 27.
27. Remove the diafiltration solution and store at 5±3° C. Combine the filtrates from Line #26 which contained OCD, and put back into the diafiltration apparatus. Concentrate down to a concentration of no more than 3.5 mg/mL. Carry out Lines # 25 and # 26.
28. Filter the product (feed) solutions from Lines # 25 and # 27 through sterile 0.45 micron filter membrane and store at 5±3° C. Rinse the diafiltration apparatus with (2×100 mL) water and filter this using sterile 0.45 micron filter membrane. Combine the rinse solution with the product solution. Take sample for HPLC analysis. Proceed to Lyophilization. Note: It is very important to use a 0.45 micron filter to avoid protein loss.

Lyophilization

Follow procedure for operating shelf dry freeze dryer or use a manifold lyophilzer (for trials).

Tray Lyophilization

29. Pour filtered product solution into a clean tray or stainless steel tray and cover the tray with clean aluminum foil, make pin holes on the surface of the foil to allow vacuum contact. Insert a thermocouple probe into the product solution and another probe at the bottom of the tray.

| Pre-Freeze Ramp Settings | | | |
|---|---|---|---|
| | Temp Deg C. | Time | RampHold |
| Step #1 | −40.0 | 60.0 | R |
| Step #2 | −40.0 | 60.0 | H |
| Step #3 | −40.0 | 60.0 | H |
| Step #4 | −40.0 | 60.0 | H |

| | | |
|---|---|---|
| Freeze Temperature | −40.0 | Degrees C. |
| Additional Freeze | 50 | Minutes |
| Power Outage | 10 | Minutes |
| Condenser Setpoint | −80.0 | Degrees C. |
| Vacuum Setpoint | 200 | Millitorr |
| Vacuum Safety | 800 | Millitorr |

| | Temp Deg C. | Vacuum | Time | RampHold |
|---|---|---|---|---|
| Set # 1 | −40.0 | 200.0 | 50.0 | H |
| Set # 2 | −10.0 | 200.0 | 360.0 | R |
| Set # 3 | −10.0 | 200.0 | 1800.0 | H |
| Set # 4 | 10.0 | 200.0 | 720.0 | R |
| Set # 5 | 10.0 | 200.0 | 1500.0 | H |
| Set # 6 | 25.0 | 200.0 | 15.0 | R |
| Set # 7 | 25.0 | 200.0 | 60.0 | H |
| Set # 8 | 25.0 | 200.0 | 0.0 | |

At this stage the product and shelf temperature should be equal at 25° C. If not, continue to dry until product and shelf temperatures are equal.

31. Overall net yield: >50% OCD (protein).

What is claimed is:

1. A substantially monodispersed calcitonin oligomer conjugate mixture consisting of a salmon calcitonin coupled to two oligomer subunits, wherein each oligomer comprises a polyalkylene glycol moiety, wherein the conjugate consists of a first oligomer subunit and a second oligomer subunit wherein the first oligomer subunit is covalently coupled to $Lys^{11}$ of the calcitonin drug and the second oligomer subunit is covalently coupled to $Lys^{18}$ of the calcitonin drug, wherein the substantially monodispersed calcitonin drug-oligomer conjugate consisting of the structure of Formula I:

$$\text{Calcitonin drug} - \left[ \begin{matrix} O \\ \| \\ C \end{matrix} - (CH_2)_x - (OC_2H_4)_y OCH_3 \right]_z \quad \text{(Formula I)}$$

wherein x is an integer from 5 to 9;

y is an integer from 4 to 10; and z is 2 which is the number of conjugation sites on the calcitonin.

2. The conjugate according to claim 1, wherein the calcitonin drug is salmon calcitonin.

3. The conjugate according to claim 1, wherein the oligomer is covalently coupled to an amine function of the calcitonin drug.

4. The conjugate according to claim 1, wherein the oligomer consist of a first oligomer and a second oligomer subunit, and wherein the first oligomer subunit and second oligomer subunit can be the same or different.

5. The conjugate according to claim 1, wherein x is from 7 to 9.

6. The conjugate according to claim 1, wherein y is from 4 to 8.

7. The conjugate according to claim 1, wherein x is 7 and y is 7.

8. A pharmaceutical composition comprising the conjugate mixture of claim 1; and a pharmaceutically acceptable carrier.

9. The pharmaceutical composition according to claim 8, wherein the oligomer is covalently coupled to an amine function of the calcitonin drug.

10. The pharmaceutical composition according to claim 8, wherein x is 9, y is 7, and z is 2.

11. The pharmaceutical composition according to claim 8, wherein x is 6, y is 8, and z is 2.

12. A method of treating a bone disorder in a subject in need of such treatment, said method comprising:

administering an effective amount of the calcitonin drug-oligomer conjugate according to claim 1 to the subject to treat the bone disorder.

13. The method according to claim 12, wherein the administration is oral.

* * * * *

UNITED STATES PATENT AND TRADEMARK OFFICE
CERTIFICATE OF CORRECTION

| | | |
|---|---|---|
| PATENT NO. | : 7,713,932 B2 | Page 1 of 1 |
| APPLICATION NO. | : 10/166355 | |
| DATED | : May 11, 2010 | |
| INVENTOR(S) | : Nnochiri N. Ekwuribe et al. | |

It is certified that error appears in the above-identified patent and that said Letters Patent is hereby corrected as shown below:

Cancel Column 36, lines 1-2

Col. 36, line 33, add the following Claim 14,

14. A monodispersed calcitonin-oligomer conjugate comprising salmon calcitonin coupled to two oligomer subunits, wherein each oligomer consists of the following structure:

$$-\overset{\overset{O}{\|}}{C}-(CH_2)_7-(OC_2H_4)_7OCH_3$$

and wherein the first oligomer subunit is covalently coupled to $Lys^{11}$ of said salmon calcitonin and the second oligomer is covalently coupled to $Lys^{18}$ of said salmon calcitonin.

Signed and Sealed this
Fourteenth Day of June, 2011

David J. Kappos
*Director of the United States Patent and Trademark Office*